(12) United States Patent
Koswara et al.

(10) Patent No.: US 10,751,685 B2
(45) Date of Patent: Aug. 25, 2020

(54) SYSTEMS AND METHODS FOR PRODUCING A CHEMICAL PRODUCT

(71) Applicant: Purdue Research Foundation, West Lafayette, IN (US)

(72) Inventors: Andy Koswara, West Lafayette, IN (US); Zoltan Kalman Nagy, West Lafayette, IN (US); Conor Douglas Parks, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 13 days.

(21) Appl. No.: 16/094,091

(22) PCT Filed: Apr. 24, 2017

(86) PCT No.: PCT/US2017/029062
§ 371 (c)(1),
(2) Date: Oct. 16, 2018

(87) PCT Pub. No.: WO2017/192286
PCT Pub. Date: Nov. 9, 2017

(65) Prior Publication Data
US 2019/0176122 A1 Jun. 13, 2019

Related U.S. Application Data

(60) Provisional application No. 62/330,425, filed on May 2, 2016.

(51) Int. Cl.
*B01J 19/00* (2006.01)
*C07C 213/06* (2006.01)
*C07D 207/16* (2006.01)

(52) U.S. Cl.
CPC ......... *B01J 19/0093* (2013.01); *C07C 213/06* (2013.01); *C07D 207/16* (2013.01);
(Continued)

(58) Field of Classification Search
CPC .......... B01J 19/0093; B01J 2219/00792; B01J 2219/00783; B01J 2219/00873;
(Continued)

(56) References Cited

U.S. PATENT DOCUMENTS

| 5,656,155 A | 8/1997 | Norcross et al. |
| 6,068,751 A | 5/2000 | Neukermans |

(Continued)

OTHER PUBLICATIONS

Acke, 2007, Evaluation of Microreactor Technology for Multicomponent Reactions, Ghent University.
(Continued)

*Primary Examiner* — Lessanework Seifu
(74) *Attorney, Agent, or Firm* — Brown Rudnick LLP; Adam M. Schoen

(57) ABSTRACT

The invention generally provides systems and methods for producing a chemical product. In certain embodiments, the invention provides systems that include a chemical product production unit. The chemical production unit includes a plurality of microfluidic modules configured to be fluidically coupled to each other in an arrangement that produces a chemical product from an input of a plurality of starting reagents that react with each other due to conditions within the plurality of microfluidic modules through which the starting reagents flow. The system also includes a droplet dispenser fluidically coupled to the chemical product production unit that forms and dispenses droplets of the chemical product.

18 Claims, 15 Drawing Sheets

(52) U.S. Cl.
CPC .............. B01J 2219/0081 (2013.01); B01J 2219/0088 (2013.01); B01J 2219/0097 (2013.01); B01J 2219/00783 (2013.01); B01J 2219/00792 (2013.01); B01J 2219/00813 (2013.01); B01J 2219/00867 (2013.01); B01J 2219/00873 (2013.01); B01J 2219/00891 (2013.01); B01J 2219/00905 (2013.01); B01J 2219/00909 (2013.01); B01J 2219/00916 (2013.01); B01J 2219/00954 (2013.01); B01J 2219/00959 (2013.01); B01J 2219/00968 (2013.01); B01J 2219/00986 (2013.01); B01J 2219/00995 (2013.01); B01J 2219/00997 (2013.01)

(58) Field of Classification Search
CPC .... B01J 2219/00968; B01J 2219/00997; B01J 2219/00909; B01J 2219/0095; B01J 2219/0097; B01J 2219/0081; B01J 2219/00916; B01J 2219/00995; B01J 2219/0088; B01J 2219/00986; B01J 2219/00891; B01J 2219/00905; B01J 2219/00954; B01J 2219/00813; B01J 2219/00867; B01J 2219/00869; B01J 2219/00871
See application file for complete search history.

(56) References Cited

U.S. PATENT DOCUMENTS

| | | | |
|---|---|---|---|
| 6,828,143 B1 * | 12/2004 | Bard | B01J 19/0093 422/129 |
| 9,562,837 B2 | 2/2017 | Link | |
| 2007/0141593 A1 | 6/2007 | Lee et al. | |
| 2008/0095705 A1 * | 4/2008 | Virtanen | B01F 13/0062 424/9.1 |
| 2008/0107935 A1 | 5/2008 | Degertekin et al. | |
| 2009/0005254 A1 | 1/2009 | Griffiths et al. | |
| 2011/0177494 A1 | 7/2011 | Ismagilov et al. | |
| 2013/0183659 A1 | 7/2013 | Link et al. | |
| 2014/0045704 A1 | 2/2014 | Jovanovich et al. | |
| 2014/0202546 A1 | 7/2014 | Ismagilov et al. | |
| 2015/0203416 A1 | 7/2015 | Van Dam et al. | |

OTHER PUBLICATIONS

Alomari, 2015, 494:568-577 Personalised dosing: Printing a dose of one's own medicine, International Journal of Pharmaceutics, 494:568-577.
Andrukh, 2011, Wire-in-a-Nozzle as a New Droplet-on-Demand Electrogenerator, Langmuir, 27:3206-3210.
Chabner, 2011, Drug Shortages—A Critical Challenge for the Generic-Drug Market, NE J Med, 365.23:2147-2149.
Chen, 2009, Design, fabrication and characterization of nano-filters in silicon microfluidic channels based on MEMS technology, Electrophoresis, 30:3168-3173.
Dittrich, 2006, Lab-on-a-chip: microfluidics in drug discovery, Nature Reviews Drug Discovery 5(3):210-218.
Duffy, 1998, Rapid Prototyping of Microlluidic Systems and Poly(dimethysiloxane), Anal. Chem, 70:4974-4980.
Fan, 2008, Develolpment of a drop-on-demand droplet generator for one-drop-fill technology, Sensors and Actuators A: Physical, 147(2): 649-655.
Fiedler, 1998, Dielectrophoretic Sorting of Particles and Cells in a Microsystem, Anal. Chem., 70:1909-1915.
Fulwyer, 1974, Electronic Separation of Biological Cells by Volume, Science, 150:910-911.
Harris, 2015, A low-cost, precise piezoelectric droplet-on-demand generator, Exp Fluids, 56:83.
Icten, 2015, Dropwise Additive Manufacturing of Pharmaceutical Products for Melt-Based Dosage Forms, Journal of Pharmaceutical Sciences, 104:1641-1649.
International Preliminary Report on Patenability, PCT/US2017/029062, 6 pages.
International Search Report and Written Opinion, PCT/Us17/29062, dated Aug. 7, 2017, 8 pages.
Jahnisch, 2004, Chemistry in Microstructured Reactors, Angew. Chem. Int. Ed., 43(4):406-446.
Jakiela, 2014,Generation of Nanoliter Droplets on Demand at Hundred-Hz Frequencies, Micromachines, 5:1002-1011.
Jayachandran, 2015, Model-Based Individualized Treatment of Chemotherapeutics: Bayesian Population Modeling and Dose Optimization, PloS one, 10(7):e0133244.
Koswara, 2014, Robustness of controlled quantum dynamics, Physical Review A 90:043414.
Koswara, 2015, Anti-Fouling Control of Plug-Flow Crystallization via Heating and Cooling Cycle, IFAC-PapersOnLine, 48-8:193-198.
Li, 1997,Transport, Manipulation, and Reaction of Biological Cells On-Chip Using Electrokinetic Effects, Anal. Chem., 69:1564-1568.
Li, 2015, Miniaturised medium pressure capillary liquid chromatography system with flexible open platform design using off-the-shelf microfluidic components, Analytica Chimica Acta, 896:166-176.
Mascia, 2013, End-to-End Continuous Manufacturing of Pharmaceuticals: Integrated Synthesis, Purification, and Final Dosage Formation, Angew. Chem. Int. Ed., 52(47):12359-12363.
Miralles, 2013, A Review of Heating and Temperature Control in Microfluidic systems: Techniques and Applications, Diagnositics (Basel), Mar.;3(1):33-67.
Nagy, 2008, Modelling and control of combined cooling and antisolven crystallization processes, Journal of Process Control, 18:856-864.
Pamme, 2003, Counting and sizing of particles and particle agglomerates in a microfluidic device using laser light scattering: application to a particle-enhanced immunoassay, Lab Chip, 3(3), 187-192.
Pennemann, 2004, Benchmarking of Microreactor Applications, Organic Process Research & Development, 8(3):422-439.
Poe, 2005, Solving the Clogging Problem: Precipitate-Forming Reactions in Flow, Angew. Chem. Int. Ed., 45:1544-1548.
Sahay, 2011, Automated Drop-on-Demand System with Real-Time Gravimetric Control for Precise Dosage Formulation, Journal of Laboratory Automation, 18(2): 152-160.
Togashi, 2009, Microreactor System Using the Concept of Numbering-Up, New Trends in Fluid Mechanics Research, Springer Berlin Heidelberg, 678-681.
Unger, 2000, Monolithic Microfabricated Valves and Pumps by Multilayer Soft Lithography, Science, 288:113-116.
Whitesides, 1998, Soft Lithography, Angew. Chem. Int. Ed., 37:550-575.
Xu, 2005, Generation of Monodisperse Particles by Using Microfluidics: Control over Size, Shape, and Composition, Angew. Chem. Int. Ed., 44: 724-728.

* cited by examiner

SYSTEMS AND METHODS FOR PRODUCING A CHEMICAL PRODUCT

RELATED APPLICATION

The present application is a 35 U.S.C. § 371 national phase application of PCT/US2017/029062, filed Apr. 24, 2017, which claims the benefit of and priority to U.S. provisional patent application Ser. No. 62/330,425, filed May 2, 2016, the content of which is incorporated by reference herein in its entirety.

FIELD OF THE INVENTION

The invention generally provides systems and methods for researching, screening and producing a chemical product in any forms, such in liquid as well as solid dosage forms.

BACKGROUND

Current manufacturing processes of solid active pharmaceutical ingredients (API) are inconsistent, inefficient, inflexible and are partially responsible for the high cost of manufacturing and, in turn, drug products incurred on patients. Existing API production technologies are based on batch configurations, not end-to-end, not integrated, have a large footprint, lack real-time process monitoring and feedback control, and are not capable of producing dose to dose drug concentration precision as necessitated by personalized health care models in a way that follows current Good Manufacturing Protocol (cGMP).

In addition, batch process dynamics that are not observable in lab or pilot-scale, such as high shear, imperfect mixing, and large temperature gradients, may unpredictably affect the performance of the scaled-up processes in detrimental ways. These lead to variable product quality, high labor costs and suboptimal use of raw materials and inventories. Furthermore, inconsistent batch-to-batch quality can lead to entire production batches being discarded (some estimate this cost to be 25% of Big and Generic Pharma's revenue stream).

Additionally, the pharmaceutical industry as a whole suffers from expensive and slow supply chains, in part due to labor-intensive and costly offline quality testing necessitated by a lack of rigorous process analytical tools (PAT) and automated quality control algorithm implementation in industrial batch operation units. These process limitations result in at least two serious public healthcare issues, including (1) worldwide drug shortages, and (2) under- and overdosing of drug prescriptions due to insufficient liquid or solid dosage variety.

SUMMARY

The invention recognizes that no portable, modular, integrated, and scalable, end-to-end manufacturing platform, readily capable of personalized liquid and solid dosage manufacturing, exists. Rather, dosages are manufactured in predefined strengths, determined during early clinical testing, to affect the largest portion of the population, using batch-manufacturing technologies. In that manner, the invention provides a continuous end-to-end pharmaceutical manufacturing platform that includes a plurality of different microfluidic modules (e.g., microreactor, microseparator, microcrystallizer) and drop on demand (DoD) API printing technology for personalized liquid or solid dosage manufacturing. A first of its kind, unprecedented in its portability, reconfigurability, speed, and scalability and API production quality, systems and methods of the invention are able to blend together numerous different technologies for chemical product manufacturing. The claimed systems and methods bring: (1) a portable, modular, and end-to-end manufacturing platform (2) personalized dosage manufacturing devoid of big pharma supply chain inadequacies; (3) higher API synthesis yields; (4) safer device operating conditions; (5) monodisperse crystal size distributions; (6) rigorous PAT for antifouling control and product quality assurance for cGMP application; (7) agile and quick acting supply chains; and (8) micro- and milli-fluidic scale technologies with an algorithmic approach to scale-up.

In certain aspects, the invention provides systems for producing a chemical product (e.g., an active pharmaceutical ingredients (API)) that include a chemical product production unit. The system can also be used for screening a variety of chemical pathways prior to production of the chemical product. The chemical screening and production unit may include a plurality of microfluidic modules configured to be fluidically coupled to each other in an arrangement that produces a chemical product. Specifically, the chemical product is produced via starting reagents that react with each other due to conditions within the plurality of microfluidic modules through which the starting reagents flow. The chemical product is then isolated through a plurality of microfluidic separation modules. The system also includes a droplet dispenser fluidically coupled to the chemical product production unit that forms and dispenses droplets of the chemical product. To achieve the production of various chemical products, the plurality of microfluidic modules may be reconfigured. The system may also include one or more pumps to drive flow (either continuous or discontinuous (e.g., intermittent) flow) through the system.

Systems of the invention can additionally include a controller that may be running one or more programs. The systems of the invention may optionally also include one or more sensors, either operably coupled to the different components of the system or integrated into the microfluidic modules of the chemical production unit. In certain embodiments, the controller is configured to receive data from the sensors that allow the controller to monitor and optimize a process occurring in one or more of the microfluidic modules. The controller may also be configured to adjust one or more parameters within one or more of the microfluidic modules based on the received data. In certain embodiments, the chemical product is a pharmaceutical drug and the controller includes a program that determines an optimal drug dosage to be dispensed by the droplet dispenser based on a patient's medical history that is received to the controller.

The microfluidic modules are designed, chosen, and arranged based on the particular chemical product to be formed. In certain embodiments, the plurality of microfluidic modules include two or more reaction microfluidic modules, a purification microfluidic module, a concentration microfluidic module, and a formulation microfluidic module.

Other aspects of the invention provide methods for producing a chemical product that involve providing a system comprising a chemical product production unit that includes a plurality of microfluidic modules and one or more droplet dispensers fluidically coupled to the chemical product production unit, introducing a plurality of starting reagents to the chemical product production unit, flowing the starting reagents through the chemical product production unit, such that a portion of a reaction occurs in each of the plurality of microfluidic modules in order to form a chemical product, and dispensing a droplet of the chemical product using the one or more droplet dispenser in liquid or solid form.

DETAILED DESCRIPTION

When compared to the current body of scientific knowledge regarding pharmaceutical manufacturing, the 20th century model of centralized, mass-producing dosage forms targeted for the general population is becoming increasingly antiquated. When viewed holistically, scientific advances in continuous manufacturing for more economical and portable drug production, genomic testing and control models for personalized health care models, and inkjet printing technologies seem to be diverging from the current blockbuster model to patient specific, lower volume, near administration site, and on-demand production models. In addition, as there are a variety of routes that become accessible in flow chemical production, it is essential to have research and development capability to screen these pathways efficiently prior to scale-up.

Figure 1A:
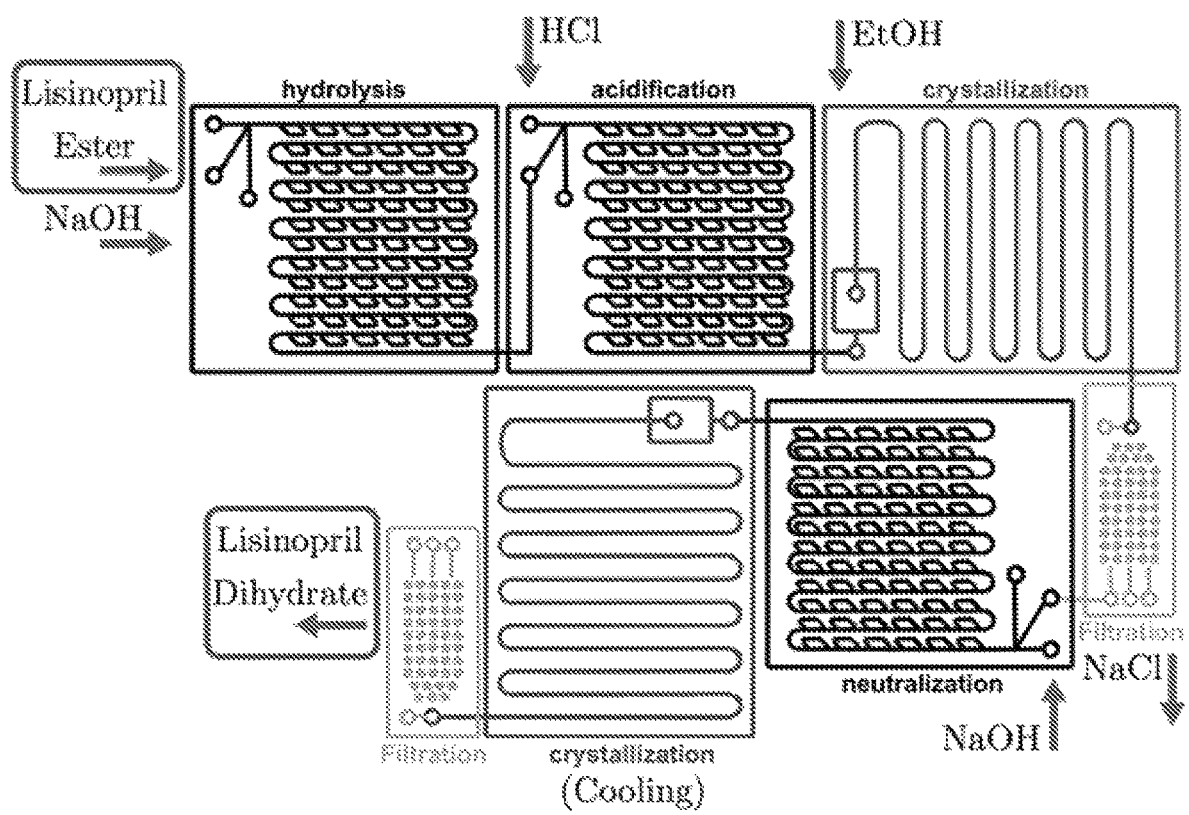
FIGS. 1A-D are an illustration of an exemplary embodiment of a system of the invention.
Figure 1B:
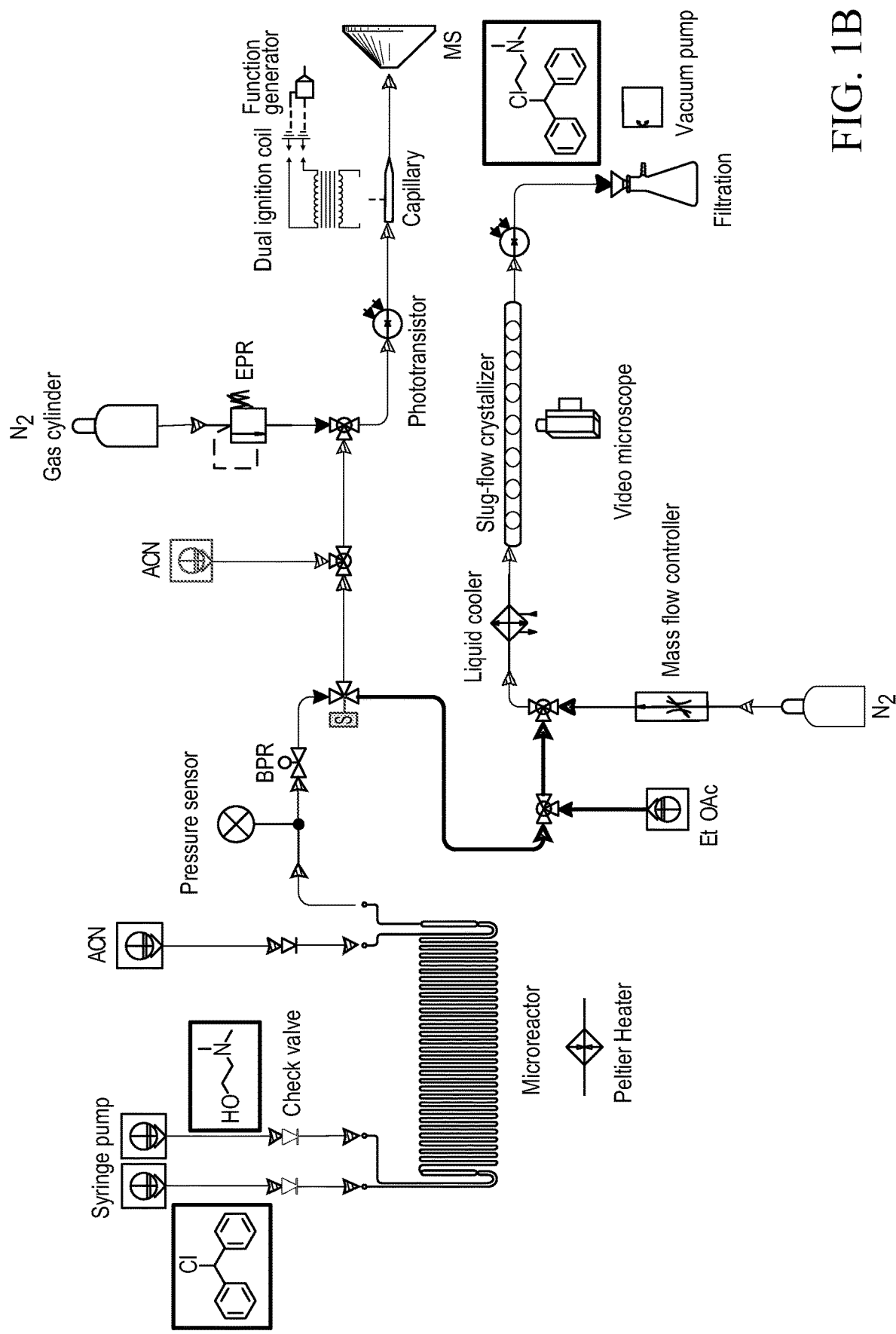
Figure 1C:
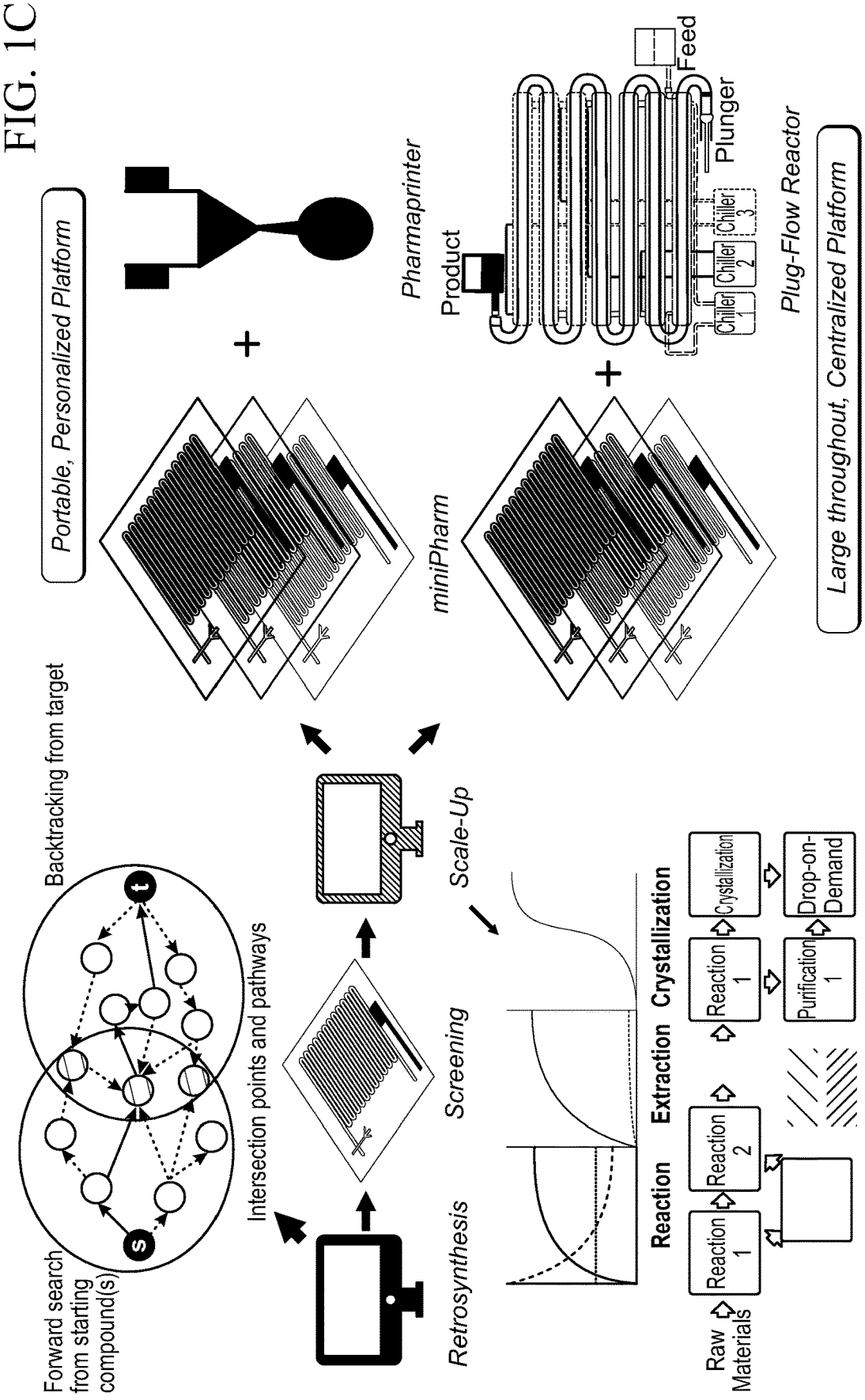
Figure 1D:
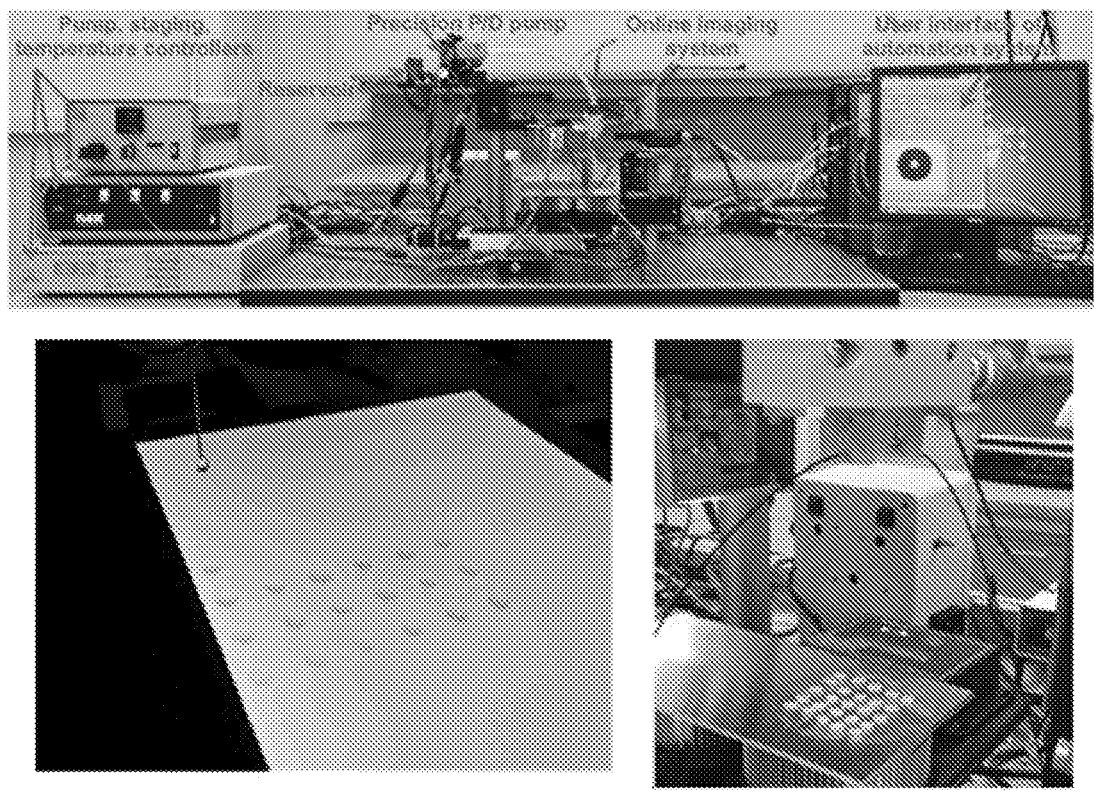

FIGS. 1A-D illustrate an exemplary embodiment of systems of the invention that provide for continuous end-to-end manufacturing of a chemical product (e.g., an active pharmaceutical ingredients (API)). As shown in FIGS. 1A-B, the systems of the invention include a chemical product production unit. The chemical production unit includes a plurality of microfluidic modules configured to be fluidically coupled to each other in an arrangement that produces a chemical product from an input of a plurality of starting reagents that react with each other due to conditions within the plurality of microfluidic modules through which the starting reagents flow. The system also includes a droplet dispenser fluidically coupled to the chemical product production unit that forms and dispenses droplets of the chemical product (FIGS. 1C-D). Fluids can be in liquid or gas form.

Figure 2:
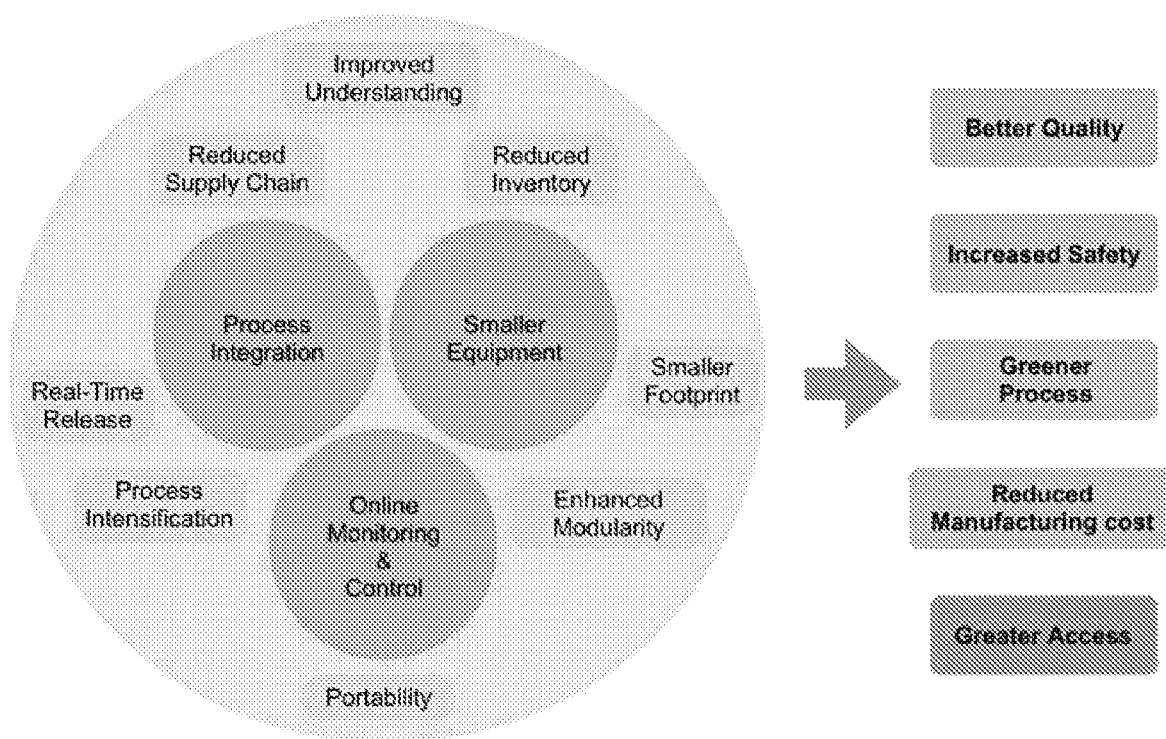
FIG. 2 is a diagram showing a holistic view of the advantages of continuous manufacturing over batch manufacturing.

According to certain embodiments of the invention, an integrated microfluidic manufacturing platform, with process sensors, controllers and actuators, as well as online PAT, represents a paradigm shift from conventional large batch manufacturing technologies with offline API quality testing. Advantages of systems and methods of the invention are shown in FIG. 2. Microfluidic devices are platforms generally having microchannels of micrometer to millimeter dimensions allowing the precise handling of nanoliter to microliter fluid volumes. Being roughly 1000 times thinner than a human hair, Microfluidic devices (MFDs) offer a 2-3 orders of magnitude increase in the surface area to volume ratio of the device when compared to its batch reactor/crystallizer counterpart. The rapid heat and mass transfer present in MFDs, due to the large surface area to volume ratios, offers a suite of advantages. From an API reaction synthesis perspective, the rapid heat and mass transfer present in continuous flow microreactor devices allows for (1) handling of previously inaccessible highly exothermic and highly pressurized reaction pathways; (2) reduced reactions times; (3) higher yields, due to the minimization of side reactions; and (4) new reaction and purification pathways which are more suitable economically and greener and safer in flow. From a crystallization perspective, MFDs provide homogeneous crystallization environments, leading to monodisperse crystal size distributions with particles on the order of tens of micrometers in size. This not only renders costly downstream units such as milling unnecessary, but leads to consistent API tablet to API tablet reproducibility in key product quality parameters such as bioavailability and dissolutions profiles.

To meet the desired demand for a particular API, the device can be parallelized in a "numbering up" approach, where devices are simply operated in parallel to achieve the desired throughput. As every device is identical, data gathered in small-scale bench top experiments now apply directly to large scale manufacturing. Thus, the need for costly scale up experiments has been eliminated. In a current drug development process, engineering knowledge, gleaned from bench- and pilot-scale experiments, does not directly translate to manufacturing scale due to scale-up nonlinearities; including shear, mixing, and heat transfer phenomena. A further complication is that different scale up criteria cannot be met simultaneously. Ideally, the driving force for crystallization, including the solute mass transfer between liquid and crystal, would be identical at all length scales. Also, shear forces imparted by the agitator would be equal, and the Reynold's number ($R_e$) and Froude number ($F_r$) would be equivalent. However, these are often competing objectives in the scale-up design of batch processes. These constraints and uncertainties inevitably lead to costly and time-consuming experiments required to ensure process robustness at various stages of the drug development process. In addition to superior product quality, control, and ease of scale up, the size of the device allows for unprecedented portability and reconfigurability. This allows the device to be transported to anywhere in the world, and be quickly assembled to meet the pharmaceutical demand.

Despite the numerous benefits associated with microfluidic devices, their commercialization for crystallization and precipitation reaction applications has been limited due to fouling. As solid (by)products adhere to the wall of the micro chambers, the flow channel is reduced leading to increased pressure drop and ultimately complete blockage rendering the device inoperable. Current attempts at mitigating fouling include periodic plunging of the device when clogged, and the use of carrier droplets in a dispersed phase to mitigate API-wall interactions. However, neither of these methods always work, and dynamic antifouling schemes need to be implemented for automated reliable manufacturing. Robust control theory provides these necessary tools, allowing the manipulation of process parameters extending from quantum to macro length scales. In certain embodiments, the systems of the invention uses the power of robust control theory to employ a novel active feedback control method (anti-fouling control) to periodically remove fouling and simultaneously ensuring that output product quality is within specifications during the whole duration of the process. In other embodiments, the systems of the invention uses air-segmentation to control the extent of crystallization within each droplet so as to prevent fouling to occur in the first place.

To this point, the benefits of continuous manufacturing have been illuminated, however the question of personalized dosage manufacturing remains. In the absence of personalized medicine, patient therapy frequently becomes suboptimal. In the case of Fluoxetine (PROZAC), for example, a 20 mg dose was chosen because it displayed an effect in 64% of the population. However, 54% of the population demonstrated a beneficial response at 5 mgs (Alomari et al., *International journal of pharmaceutics* 494.2 (2014): 568-577; the content of which is incorporated by reference herein in its entirety). Furthermore, the lower dose has fewer negative side effects reported. Against this knowledge, DoD printing technology is promising in that it is capable of dispensing predictable, and highly controllable, API dosage droplets onto edible substrates for consumption. By changing the drop size and formulation, the dosage can be specifically tuned to a patient's needs. However, in the absence of the API synthesis and crystallization steps implemented with the printer, the DoD device is still dependent on the sluggish and slow supply chains of pharma for API production. However, an integrated continuous end-to-end API synthesis, crystallization, and ink jet printing unit as provided by the invention allows for personalized medicine production anywhere in the world in rapid response to surges in demand.

To this end, the invention provides a portable, drop-on-demand, miniaturized continuous end-to-end pharmaceutical manufacturing platform for production of a drug product with personalized dosages (Drop-on-Demand (DoD) MiniPharm). The DoD MiniPharm system may contain two classes of hardware. The first hardware component is a network of reconfigurable pharmaceutical unit operations (chemical production unit with a plurality of microfluidic modules), each of which may include specially engineered microfluidics, allowing for fluid dynamics to perform highly reproducible, controllable, and previously inaccessible flow chemistries to produce a chemical product, such as a solid API. The unit operation is also specifically designed to be a module that can be flexibly switched in and out depending on real-time medical demand. The second hardware component is a drop-on-demand (DoD) module that may be based on inkjet printing technology that manufactures the final drug product composed of the API as well as its excipients. The DoD module enables personalized dosage of solvent-based or melt-based API. The API is first synthesized and separated in the upstream microfluidic module(s), and is then deposited onto an edible substrate, such as a polymeric film or placebo tablet, in a continuous or discontinuous manner, using the DoD ink jet printing technology. Subsequently, liquid excipients may then be added on a layer-by-layer basis, if needed for application. By nature of continuous flow-processes, each module in the DoD MiniPharm platform is exceptionally scalable, whereby modules can be added in parallel by numbering up the constitutive units in order to increase throughput. Additionally, stacks of processing units, of various sizes and configuration, can be combined together to produce combination APIs. The DoD MiniPharm system is also equipped with at least three classes of software, namely (1) an advanced real-time process monitoring and control algorithm, allowing for antifouling feedback control, as well as (2) a state-of-the-art algorithm for determining optimal drug dosages based on the patient's medical history, and (3) a state-of-the-art algorithm that allows integration and scale-up given reaction and purification screening results obtained using the system.

Figure 3:
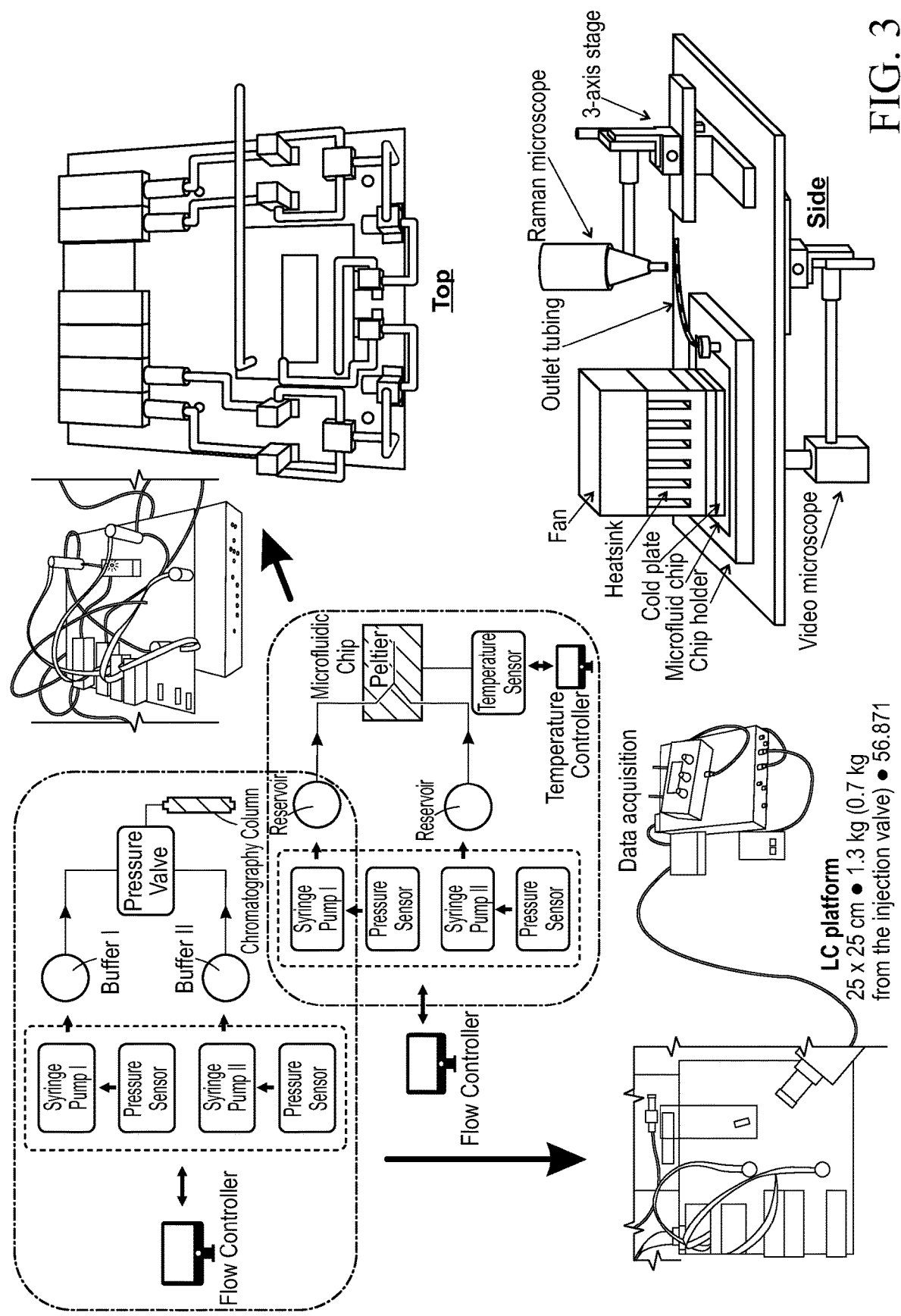
FIG. 3 is a set of illustrations of another exemplary embodiment of a system of the invention.

In an exemplary embodiment, the system includes a combination of micro- (MFD) and milli-fluidic (MLD) chips and tubing with interchangeable modules in terms of channel dimensions, flow geometry, and inter-connections between the different functional parts of the devices (FIGS. 1A-B and FIG. 3). Each chip and tubing is designed for a specific function, such as reaction, purification, concentration and formulation all integrated for the on-demand manufacturing of an API. Both homogenous and heterogeneous reactions are considered which are suitable for flow application, including gas, liquid, air-segmented solid-liquid, packed-bed solid phase reactions, as well as a mixture of packed-bed solid with gas and packed-bed solid with liquid phase reactions. These reactions are designed and optimized with respect to the starting materials and operating conditions, such as temperature, pressure and flow rates so as to not readily clog the reactor during the flow process. The separation processes may include inorganic and organic phase separation, liquid-liquid extraction, membrane extraction, chromatography, crystallization, precipitation, concentration and filtration. Specifically, the concentration step is accomplished via distillation, evaporation, or (droplet) crystallization followed by filtration while the formulation step is accomplished via droplet crystallization or drop-on-demand technology.

As a result, the systems and methods of the invention represent a revolution from a non-personalized, disconnected, batch drug product manufacturing process towards personalized continuous manufacturing platform that provides for real time implementation in manufacturing facilities, hospitals and emergency locations, such as the case in Ebola outbreaks. Systems and methods of the invention bring a competitive advantage in not only the quality and economics of the drugs produced, but also the flexibility and agility for real-time product release to overcome development, manufacturing, and supply chain challenges, such as drug surplus and shortage, and incompatible drug dosages.

Figure 4A:
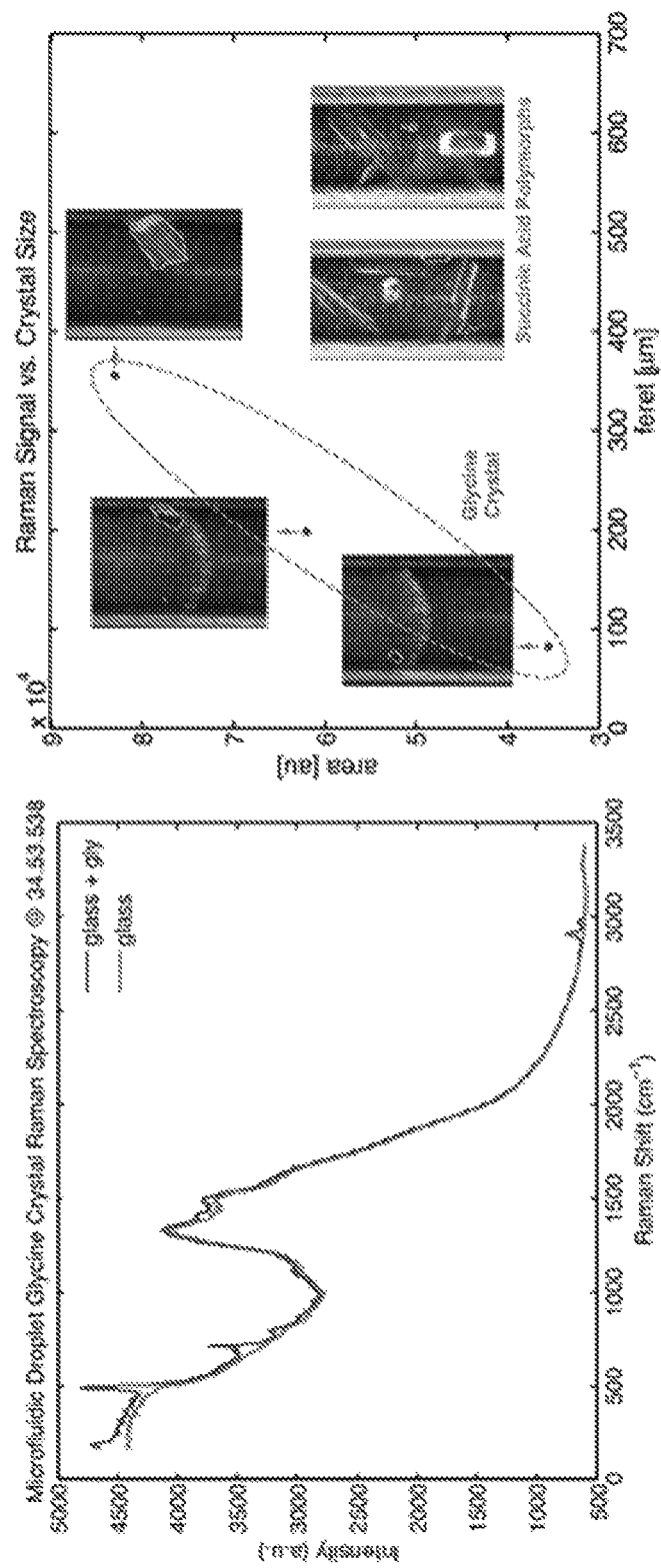
FIG. 4A shows an example of monitoring within the system. The figure shows coupling of real-time Raman Spectroscopy with the microcrystallizer. This serves as an example of the many PAT tools, which can be implemented in the systems and methods of the invention.

Each functional part of the device may include an MFD/MLD chip or tubing connected to a set of actuators, including valves, flow controllers, pumps, etc., sensors, such as flow rate sensor, pressure sensor, thermocouple, and heat transfer elements, including but not limited to a Peltier element, and reservoirs. The reservoirs collectively act as buffer elements between the different steps to seamlessly connect the processes, which have various volumetric throughputs, such that continuous flow may be achieved throughout the device (although discontinuous flow/stop flow, may also be used within the systems and methods of the invention). The materials of equipment are chosen with the appropriate chemical compatibility under different temperature and pressure rating specific to each process. Additionally, the choice of pumps implemented in the device, such as syringe, peristaltic and rotary pump, ranges from a nL to a mL in flow rates and 10 to 10,000 psi in pressure depending on the flow and pressure requirements for the different functions. At least one, and sometimes a plurality or all steps during the manufacturing process are monitored for product characteristics (e.g. purity and polymorphic forms) using a variety of inline process analytical tools (PAT) or miniaturized micro-total analysis system (micro-TAS), such as laser light scattering (Pamme et al., Lab on a Chip, 3(3), 187-192, 2003, the content of which is incorporated by reference herein in its entirety), UV/Vis photodetector (Li et al., Analytica chimica acta 896 (2015): 166-176, the content of which is incorporated by reference herein in its entirety), chromatography (Li et al., Analytica chimica acta 896 (2015): 166-176, the content of which is incorporated by reference herein in its entirety), and, more recently, mass spectrometry and Raman spectroscopy. FIG. 4 shows an example of monitoring within the system. The figures shows coupling of real-time Raman Spectroscopy with the microcrystallizer. This serves as an example of the many PAT tools, which can be implemented in the systems and methods of the invention.

Figure 5:
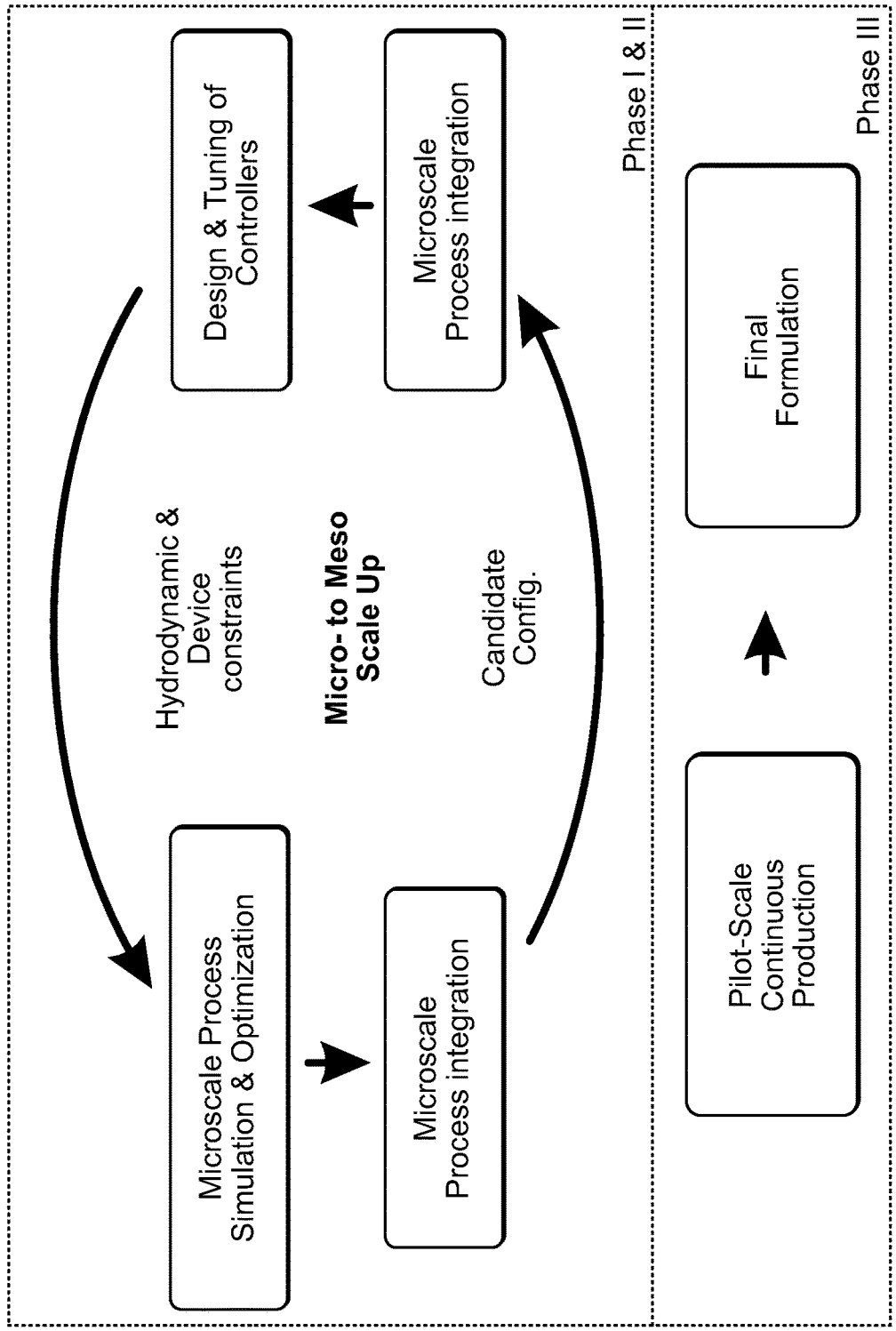
FIG. 5 is a process flow chart for scaling up systems of the invention, taking into account the different purification pathways which can be implemented given a reaction.
Figure 6:
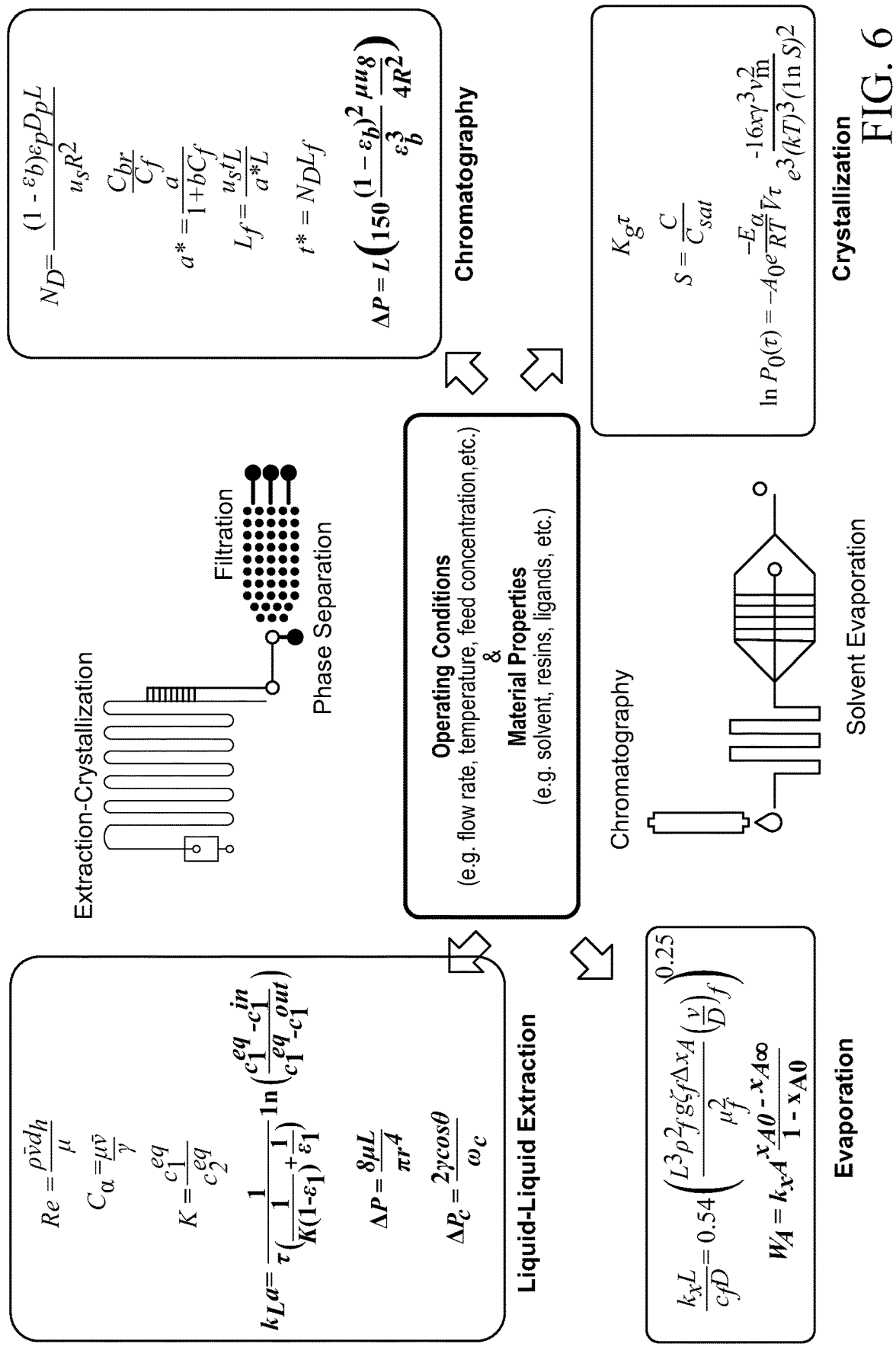
FIG. 6 is a diagram showing dimensional and dimensionless parameters for flexible process (re)configuration and scale-up.
Figure 7:
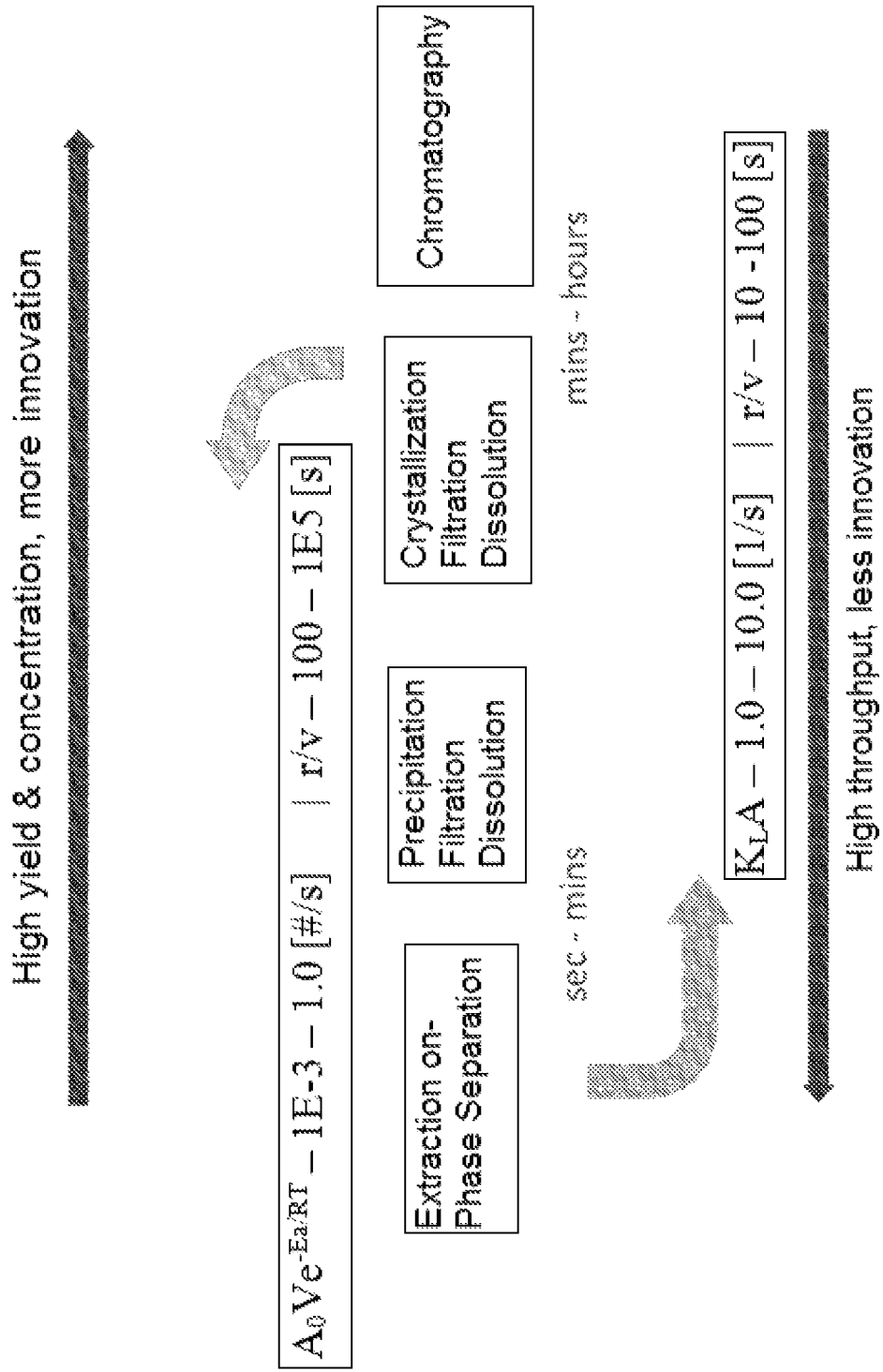
FIG. 7 is another process flow chart for scaling up systems of the invention, taking into account the different purification pathways which can be implemented given a reaction

The method of device scale-up is performed by parallel addition of MFD reactors or enlargement of the MFD reactor channels while maintaining a set of dimensionless parameters characteristic to each process constant and dimensional parameters within the upper and lower bound limit (FIGS. 5-6). Specifically, for chromatography (FIG. 6-7), this includes the ratio of intra-particle diffusion and convection rate, the dimensionless loading time, the loading factor, the ratio of axial dispersion and convection rate, the ratio of film-diffusion and convection rate, and the maximum pressure drop. For crystallization, it includes the product of residence time and crystal growth rate, the ratio of fouling rate to crystal growth rate, the relative supersaturation, and the nucleation rate. For extraction, the ratio of Reynold's to Capillary number, the product of mass transfer coefficient and residence time, the partition coefficient, the maximum pressure drop and the ratio of outlet pressure drop of organic and aqueous phase, with the effect of hydrophilic and hydrophobic capillary pressure taken into consideration. For evaporation, the ratio of convection to evaporation rate, and the product of mass transfer coefficient and residence time.

Figure 8A:
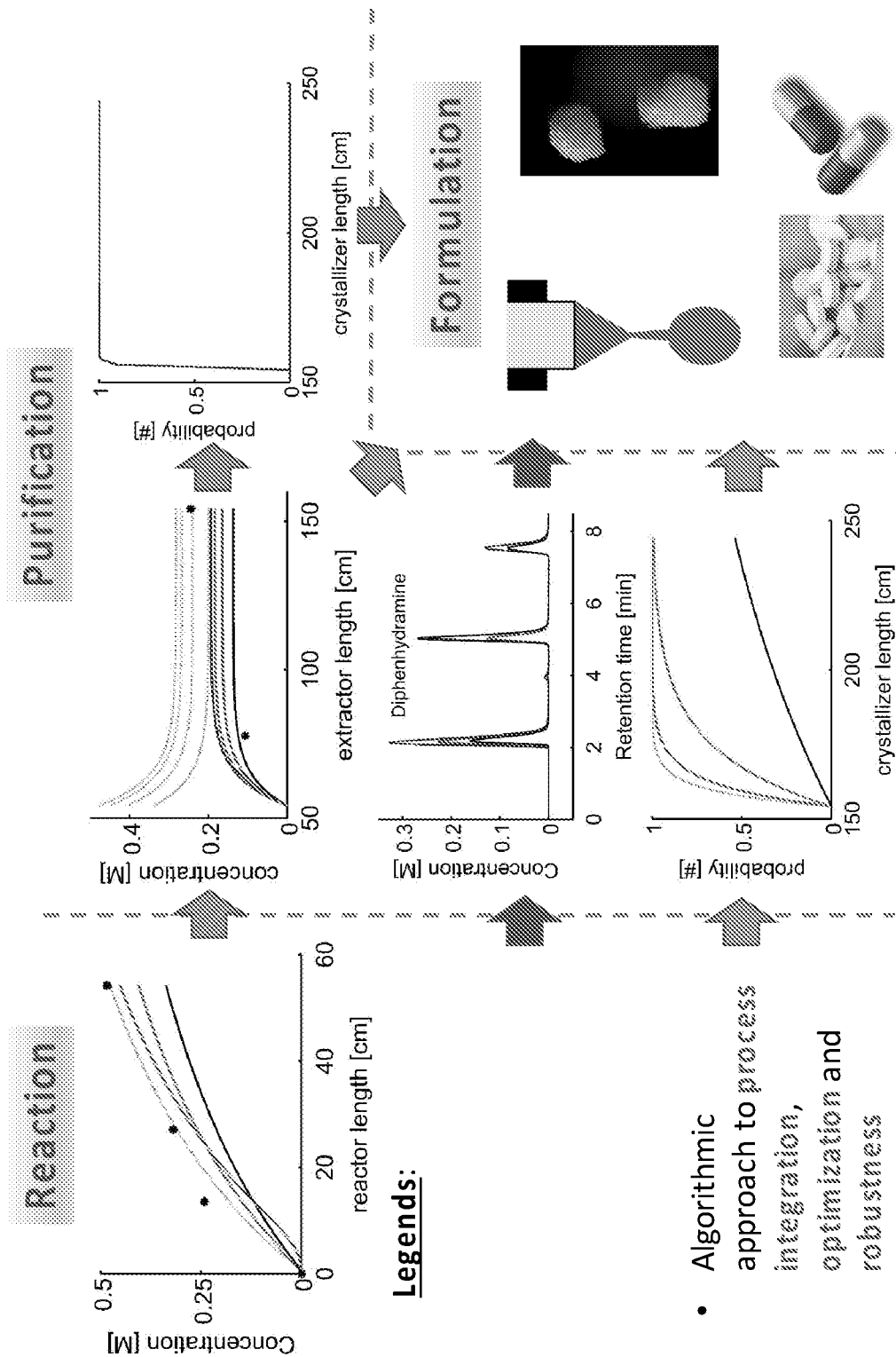
FIGS. 8A-B show a process dynamic simulation of different manufacturing processes for real-time optimization via single-shot or sequential optimization given quantitative data acquired from a variety to PAT tools, including mass spectrometry and liquid chromatography.
Figure 8B:
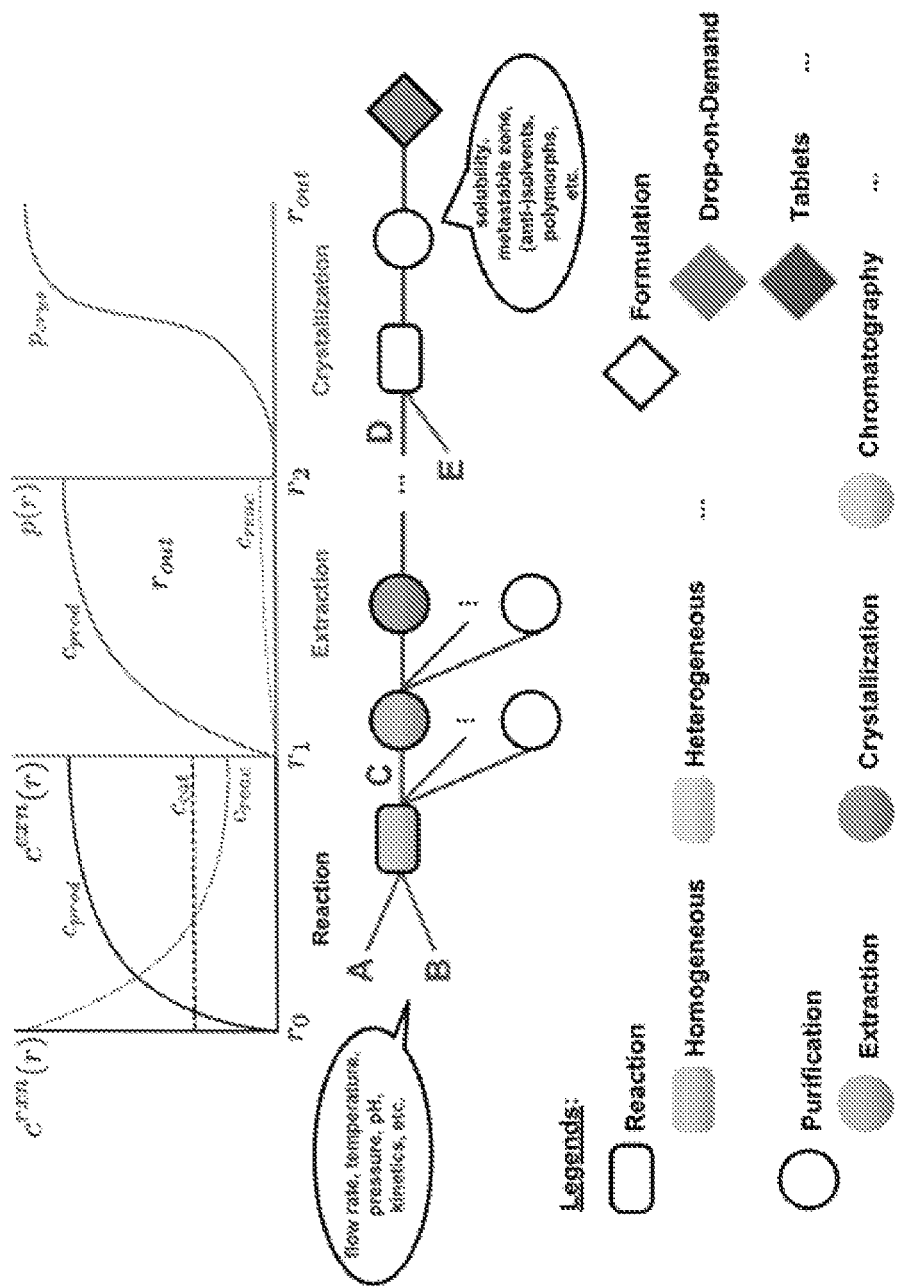

During process integration and optimization (FIGS. 8A-B), the process decision variables, including temperature, pressure, flow-rate and channel dimensions, are varied to achieve the desired trade-off between yield, purity and throughput. Throughout the optimization process, the aforementioned set of dimensionless parameters undergo an algebraic optimization with operational constraints. The operational constraints are the lower and upper bound of the decision variables. The objective function considers a combination of purity, yield and throughput operating variables. While the dimensionless parameters determine the steady-state quality of the device. The start-up quality of the device is also important as it determines the time required to reach steady state and, in turn, the productivity of the device in the form of lag-time and waste. The start-up dynamics are analyzed using both simulation and experimentation, the results of which are used to perform a start-up optimization by implementation of real-time feedback control.

The inner dimensions of the reactor's channel may range from the micrometer to the millimeter while the length of the reactor may be in the meter scale. The throughput of the device can be as low as ~10 nL/min and as high as ~1 mL/min. For a lower throughput, a chip-based MFD device is used using transparent materials with the appropriate chemical compatibility and pressure and temperature rating. For a higher throughput, a tube-based MFD device is used with the same requirements. The MFD chip is temperature-controlled using a peltier-coupled with a liquid-bath while the MFD tube is coiled around a conducting cylindrical platform, temperature-controlled using a ministat. Process integration between multiple reactor and purification modules is associated with a number of engineering and design challenges and, in turn, innovations, including:

a. Large pressure drop. A purification process may be employed which entails a large pressure drop (for e.g. chromatography) causing other operations upstream of the device to also experience high pressures. Integration design must thus ensure appropriate fittings and vent systems are used to avoid negative operational effects, such as leakage, reaction rates, etc.

b. Heat distribution/insulation. Various functions of the device require different heat energy requirements. Some reaction and purification steps would be performed at higher temperature while others at a significantly lower temperature. This necessitates that the different parts of the device be properly insulated for maintaining individual process quality.

c. Dead volume. Connections between different functions of the device via tubes, including those to the inline monitoring systems are associated with dead volume. This is to be minimized to reduce yield loss and delay in the real-time process feedback control.

d. Limit of monitoring frequency. PAT tools, such as video imaging and spectroscopy, have a latency that limits the frequency of detection measurements. The integrated process must in turn be sufficiently robust without the need for feedback control at all times.

e. Residence time matching. In addition to other operating conditions, such as pressure and flow rate, different functions of the integrated device have different residence time requirements. This is accomplished either via multiplexing of smaller reactors and/or designing reactor of various channel dimensions.

The invention represents an upgrade in chemical product manufacturing, providing flow-based pharmaceutical production technology with an unparalleled degree of consistency, speed, scalability, modularity, and portability. The microfluidic-based systems and methods of the invention in turn addresses the following key issues associated with current pharmaceutical development and manufacturing processes.

Inconsistent and labored pharmaceutical manufacturing using current batch production technologies are overcome. Conventional pharmaceutical manufacturing facilities require batch equipment to perform essential unit operations, such as reaction, crystallization and tableting. To reach large scale manufacturing production levels, large batch equipment is required. From an economics perspective, this equipment represents a sizeable capital investment. From an engineering perspective, the device is more challenging to control and monitor. Rarely are process analytical technologies (PAT's) commonly implemented in lab-scale equipment, such as FTIR, UV/VIS, PVM, and FBRM, properly applied at production scale. Furthermore, the heterogeneous environment created within batch equipment leads to batch-to-batch drug variability in terms of polymorphic form, particle size distribution, and particle morphology. This can lead to entire batches being discarded (some estimate this cost to be 25% of Big and Generic Pharma's revenue stream). Equipment down time, or an unwillingness to upgrade the batch facility due to capital investment, frequently contributes to the public health issue of drug shortages worldwide. Furthermore, batch processes usually lead to excess materials, to ensure API availability during clinical studies, which lead to a large overhead in the drug development process. This lack of flexibility and scalability in API development and manufacturing add to the already massive cost of clinical trials in the industry.

Design changes associated with scale up during different stages of drug development is addressed. In current drug development process, engineering knowledge, gleaned from bench- and pilot-scale experiments, does not directly translate to manufacturing scale due to scale-up nonlinearities, such as shear, mixing, and heat transfer phenomena. A further complication is that different scale up criteria cannot be met simultaneously. Ideally, the driving force for crystallization, including the solute mass transfer between liquid and crystal, would be identical at all length scales. Also, shear forces imparted by the agitator would be equal, and the relevant dimensionless analysis, such as Reynold's number ($R_e$) and Froude number ($F_r$), would be equivalent. However, these are often competing objectives in the scale-up design of batch processes. These constraints and uncertainties inevitably lead to costly and time-consuming experiments required to ensure process robustness at various stages of the drug development process.

Non-steady state process and emergency blockage due to fouling are overcome. Despite the numerous benefits associated with microfluidic devices, their commercialization for crystallization and precipitation reaction applications has been limited due to fouling. As solid (by)products adhere to the wall of the micro chambers, the flow channel is reduced leading to increased pressure drop and ultimately complete blockage rendering the device inoperable. By contrast, the systems and methods of the invention employ a novel active feedback control method (anti-fouling control) to periodically remove fouling and simultaneously ensuring that output product quality is within specifications during the whole duration of the process. In addition, the systems of invention employs air-segmented droplet flow to control the degree of crystallization and precipitation to avoid fouling.

It is believed that the systems and methods of the invention offer an unparalleled degree of understanding and control over a large range of operating conditions when compared to the aforementioned API production technologies. MSMPR, OBR and IJR have characteristic length scales 1 to 6 orders of magnitude larger than that of a microfluidic device. As a result, the systems and methods of the invention present a significantly greater surface area-to-volume ratio such that higher degree of control over material flow and temperature profiles are possible. This fact allows for greater design and control over product quality and lot-to-lot reproducibility in terms of polymorphic form, particle size distribution, and particle morphology. Furthermore, the smaller length scales allow for minimal use of reagents for drug synthesis and testing, thus reducing costs during drug development and discovery. The systems and methods of the invention are also relatively small, which means that they can utilize a lower manufacturing footprint and are significantly more portable than existing technologies. Also, existing technologies suffer from scalability issues. Specifically, scale-up always involve design change. That is not the case with the systems and methods of the invention, where scaling up simply means increasing the number of constitutive units.

Microfluidic Modules

The chemical production unit of the present invention includes one or more microfluidic modules. In certain embodiments, a microfluidic module may be a microsubstrate, e.g., a microchip. The terms microsubstrate, substrate, microchip, and chip are used interchangeably herein. Typically, a microfluidic module will include at least one of: an inlet, at least one channel, at least one reservoir, and/or at least one outlet. The skilled artisan will recognize that a subset of these can be used in any microfluidic module and that not all components are required to be in any single microfluidic module. Other components within a microfluidic module may include features to perform specific chemical processes, as discussed further below, along with sensors (detection sensors) and other components. It shall be appreciated that the modules and channels are in fluid communication with each other and therefore may overlap; i.e., there may be no clear boundary where a module or channel begins or ends. A plurality of microfluidic modules of the invention may be combined in one chemical production unit.

The dimensions of the substrate are those of typical microchips, ranging between about 0.5 cm to about 25 cm per side and about 1 micron to about 1 cm in thickness. A substrate can be transparent and can be covered with a material having transparent properties, such as a glass coverslip, to permit optical detectors or optical sensors (e.g., an optical device such as an optical microscope) to be integrated with microfluidic modules. The material can be perforated for functional interconnects, such as fluidic, electrical, and/or optical interconnects, and sealed to the back interface of the microfluidic module so that the junction of the interconnects to the device is leak-proof. Such a microfluidic module can allow for application of high pressure to fluid channels without leaking.

A variety of materials and methods, according to certain aspects of the invention, can be used to form any of the described components of the systems and devices of the invention. In some cases, the various materials selected lend themselves to various methods. For example, various components of the invention can be formed from solid materials, in which the channels can be formed via molding, micromachining, film deposition processes such as spin coating and chemical vapor deposition, layer-by-layer fused deposition modeling, laser fabrication, photolithographic techniques, etching methods including wet chemical or plasma processes, and the like. See, for example, Scientific American, 248:44-55, 1983 (Angell, et al), the content of which is incorporated by reference herein in its entirety. At least a portion of the fluidic system can be formed of silicone by molding a silicone chip. Technologies for precise and efficient formation of various fluidic systems and devices of the invention from silicone are known. Various components of the systems and devices of the invention can also be formed of a polymer, for example, an elastomeric polymer such as polydimethylsiloxane ("PDMS"), polytetrafluoroethylene ("PTFE") or TEFLON (synthetic fluoropolymer of tetrafluoroethylene, Dupont Co.), or the like.

The channels within a microfluidic module can be formed, for example by etching a silicon chip using conventional photolithography techniques, or using a micromachining technology called "soft lithography" as described by Whitesides and Xia, Angewandte Chemie International Edition 37, 550 (1998), the content of which is incorporated by reference herein in its entirety. These and other methods may be used to provide inexpensive microfluidic modules, and in the case of soft lithography, can provide robust microfluidic modules having beneficial properties such as improved flexibility, stability, and mechanical strength. When optical detection is employed, the microfluidic module also provides minimal light scatter.

Different components can be formed of different materials. For example, a base portion including a bottom wall and side walls can be formed from an opaque material such as silicone or PDMS, and a top portion can be formed from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be formed as illustrated, with interior channel walls coated with another material. Material used to form various components and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device.

Various components of the microfluidic modules are formed from polymeric and/or flexible and/or elastomeric materials, and can be conveniently formed of a hardenable fluid, facilitating formation via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying formation of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

In certain embodiments, the PDMS surface is treated to be bonded with high intensity oxygen or air plasma. The process converts the top layer of PDMS to glass which bonds extremely well with normal adhesives. Tests using this method to bond external fluid lines to PDMS using a UV-cure adhesive (Loctite 352, 363, and others) resulted in a bond that is stronger than the PDMS substrate, resulting in fracture of the PDMS prior to failure of the bond. The present method combines high radiant flux, wavelength selection, and cure exposure time to significantly enhance the bond strength of the adhesive.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be formed and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," Anal. Chem., 70:474-480, 1998 (Duffy et al.), incorporated herein by reference.

Another advantage to forming microfluidic structures (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In one embodiment, a bottom wall is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

Channels

The microfluidic modules of the present invention include channels that form the boundary for a fluid. A channel, as used herein, refers to a feature on or in a substrate that at least partially directs the flow of a fluid. In some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

An open channel generally will include characteristics that facilitate control over fluid transport, e.g., structural characteristics (an elongated indentation) and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. Of course, in some cases, larger channels, tubes, etc. can be used to store fluids in bulk and/or deliver a fluid to the channel. In one embodiment, the channel is a capillary.

The dimensions of the channel may be chosen such that fluid is able to freely flow through the channel. The dimensions of the channel may also be chosen, for example, to allow a certain volumetric or linear flow rate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, etc.

The microfluidic module can also include one or more fluid channels to inject or remove fluid into another channel within a microfluidic module. The channels of the microfluidic modules can be of any geometry as described. However, the channels of the microfluidic modules can comprise a specific geometry such that the contents of the channel are manipulated, e.g., sorted, mixed, prevent clogging, etc.

A microfluidic module can also include a specific geometry designed in such a manner as to prevent the aggregation of biological/chemical material and keep the biological/chemical material separated from each other. The geometry of channel dimension can be changed to disturb the aggregates and break them apart by various methods, that can include, but is not limited to, geometric pinching (to force analytes within fluids through a (or a series of) narrow region(s)) or a barricade (place a series of barricades on the way of the moving fluid to disturb the movement and break up aggregates of analytes).

To prevent material from adhering to the sides of the channels, the channels (and coverslip, if used) may have a coating which minimizes adhesion. Such a coating may be intrinsic to the material from which the device is manufactured, or it may be applied after the structural aspects of the channels have been microfabricated. TEFLON (synthetic fluoropolymer of tetrafluoroethylene, Dupont Co.) is an example of a coating that has suitable surface properties. The surface of the channels of the microfluidic module can be coated with any anti-wetting or blocking agent. The channel can be coated with any compound to prevent adhesion of the biological/chemical sample.

Driving Forces

The microfluidic modules can use pressure driven flow control, e.g., utilizing valves and pumps, to manipulate the flow of reagents in one or more directions and/or into one or more channels of a microfluidic module. However, other methods may also be used, alone or in combination with pumps and valves, such as syringe pumps, electro-osmotic flow control, electrophoresis and dielectrophoresis (Fulwyer, Science 156, 910 (1974); Li and Harrison, Analytical Chemistry 69, 1564 (1997); Fiedler, et al. Analytical Chemistry 70, 1909-1915 (1998); U.S. Pat. No. 5,656,155). The content of each reference is incorporated by reference herein in its entirety.

Positive displacement pressure driven flow is an exemplary way of controlling fluid flow as well as dielectrophoresis. Multiple different driving forces can be used within the chemical production unit, e.g., a different driving force can be used for each microfluidic module. In certain embodiments, multiple driving forces are used in a single microfluidic module. In other embodiments, the same driving force is throughout the chemical production unit.

The pressure at the inlet of a microfluidic module can also be regulated by adjusting the pressure on the channel coupled to the inlet. For example, a valve may be placed at or coincident to the inlet to control the flow of solution into the inlet channel of a microfluidic module, thereby controlling the flow within a microfluidic module. Flow may also depend on channel diameter, the viscosity of the fluids, and shear pressure.

Without being bound by any theory, electro-osmosis is believed to produce motion in a stream containing ions e.g.

a liquid such as a buffer, by application of a voltage differential or charge gradient between two or more electrodes. Neutral (uncharged) analytes can be carried by the stream. Electro-osmosis is particularly suitable for rapidly changing the course, direction or speed of flow. Electrophoresis is believed to produce movement of charged objects in a fluid toward one or more electrodes of opposite charge, and away from one on or more electrodes of like charge.

Reservoir/Well

A microfluidic module of the invention can include a sample solution reservoir or well or other apparatus for introducing a fluid or reagent to the chemical production unit, via an inlet of one of the microfluidic modules, which is typically in fluid communication with a channel within the chemical production unit. Reservoirs and wells used for loading one or more reagents onto the chemical production unit of the present invention, include but are not limited to, chambers within the microfluidic modules. A reservoir may facilitate introduction of reagents into the chemical production unit.

Electrodes

The microfluidic module can include channels for use in fluid control and other channels filled with a metal alloy for casting integrated metal alloy components (i.e., electrodes). Alternatively, the electrodes can be manufactured using other technologies (e.g., lithographically patterned electrodes made from indium tin oxide or a metal such as platinum). The microfluidic module can include metal alloy components useful for performing electrical functions on fluids. The device can contain more than one of the above mentioned components for more than one of the above mentioned functions.

The electrodes comprising metal alloy components may either terminate at fluid channels or be isolated from fluid channels. The electrodes can be constructed by filling the appropriate channels with metal alloy. One way this can be accomplished is to use positive pressure injection of the metal alloy in a melted state, such as with a syringe, into the channels, and then cool the metal alloy to a solid form. Another example is to use negative pressure to draw the metal alloy in a melted state into the channels, and then cool the metal alloy to a solid form. This can be accomplished for example by use of capillary forces. Another method of construction can use any of the above mentioned embodiments, and then flush out the metal alloy in a melted state with another liquid to define the geometry of the metal alloy components. Another example is to use any of the above mentioned embodiments, and then use a localized cold probe to define a solid termination point for the metal alloy, and then cool the remaining metal alloy to a solid form. A further example is to use another material, such as microscopic solder spheres or UV curable conductive ink, to form a barrier between fluid and metal alloy channels, to define the geometry of the metal alloy components.

The microfluidic module can include a combination of both integrated metal alloy components and a patterned electrically conductive layer. The patterned electrically conductive layer can have features patterned such that their boundaries are within a leak-proof seal. The device can have a patterned electrically conductive feature as one of two charging electrodes and one integrated metal alloy component as the other of two charging electrodes.

To prevent leakage of fluid out of electrodes placed within microfluidic channels, the microfluidic module can include a layer patterned with channels for fluid control, and another layer with patterned electrically conductive features, where the features are patterned such that their boundaries are within a leak-proof seal. The leak-proof seal can be achieved at the interface between the unpatterned areas of the fluid control layer and the unpatterned areas of the electrically conductive layer. The leak-proof seal can also be achieved by a third interfacial layer between the fluid control layer and the unpatterned areas of the electrically conductive layer. The third interfacial layer can or cannot be perforated at specific locations to allow contact between the fluid and the electrically conductive layer. Electrical access ports can also be patterned in the fluid control layer.

Monitoring within a Microfluidic Module

The microfluidic module of the present invention can also include one or more detection elements (apparatuses, devices, components) that assist in monitoring processing occurring within the microfluidic module. A detection element is generally located within one or more microfluidic modules, typically within the channel where reagents or chemical products are to be detected, identified, measured or interrogated on the basis of at least one characteristic. The reagents or chemical products can be examined one at a time or in bulk, and the characteristic is detected or measured. Exemplary detector elements are optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement. However, other detection techniques can also be employed.

The term "determining," as used herein, generally refers to the analysis or measurement of a reagent or chemical product, for example, quantitatively or qualitatively, and/or the detection of the presence or absence of the reagent or chemical product. "Determining" may also refer to the analysis or measurement of an interaction between two or more reagents or a reagent with an intermediate of the chemical product, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements such as ionization-based mass spectrometry; optical measurements such as optical density measurements; circular dichroism; light scattering measurements such as quasielectric light scattering; polarimetry; refractometry; or turbidity measurements as described further herein.

A detection element is within, communicating or coincident with a portion of the channel at or downstream of the inlet. Precise boundaries for the detection element are not required.

In certain embodiments, the microfluidic modules include self-aligning optical waveguides and optical elements (lenses, prisms, mirrors, interconnects, etc.) for detection of reagents or chemical products and/or control of reactions. Such waveguides can be used to provide well defined optical access to the fluidic channels to permit optical scattering, absorption, fluorescence, or any other optical measurement technique.

In order to create the waveguides, a separate series of channels and useful shapes (lenses, mirrors, etc) can be created either simultaneously within the other channels in the microfluidic module (i.e. in the same processing step) or in successive steps. The reusable master created in this way can then be used to form the waveguide components and fluid channels without the need for special fixturing or careful alignment in subsequent steps. The extra channels or shapes can then be filled with a high index of refraction liquid (for waveguides) or reflective material (for mirrors) through injection into the channel or void. The liquid can either remain as a fluid or be allowed to solidify. UV cure epoxies used by the telecommunications industry are excellent choices for the waveguide materials. Possible waveguide geometry can include a focusing lens and a back-reflecting mirror.

In other embodiments, one or more sensors and/or processors may be positioned to be in sensing communication with the fluid within the channel. "Sensing communication," as used herein, means that the sensor may be positioned anywhere such that the fluid within the chemical production unit (e.g., within a channel of one or more microfluidic modules) may be sensed and/or determined in some fashion. For example, the sensor may be in sensing communication with the fluid such that the communication is fluid communication, optical or visual communication, thermal communication, pneumatic communication, electronical communication, or the like. The sensor can be positioned proximate the fluid, for example, embedded within or integrally connected to a wall of a channel, or positioned separately from the chemical production unit but with physical, electrical, and/or optical communication with the chemical production unit (e.g. one or more microfluidic modules of the chemical production unit) so as to be able to sense and/or determine one or more reagents, chemical product intermediates, and/or chemical product within the fluid. For example, a sensor may be free of any physical connection with a channel containing a fluid, but may be positioned so as to detect electromagnetic radiation arising from the fluid, such as infrared, ultraviolet, or visible light. The electromagnetic radiation may be produced by one or more reagents, chemical product intermediates, and/or chemical product within the fluid in such a manner as to indicate one or more characteristics of the fluid, for example, through absorption, reflection, diffraction, refraction, fluorescence, phosphorescence, changes in polarity, phase changes, changes with respect to time, ionization, etc. As an example, a laser may be directed towards the fluid, and the fluorescence of the fluid may be determined. "Sensing communication," as used herein may also be direct or indirect. As an example, light from the fluid may be directed to a sensor, or directed first through a fiber optic system, a waveguide, etc., before being directed to a sensor.

Non-limiting examples of detection sensors useful in the invention include optical or electromagnetically-based systems. For example, the sensor may be a fluorescence sensor (e.g., stimulated by a laser), a microscopy system (which may include a camera or other recording device), ultrasound-based system or the like. As another example, the sensor may be an electronic sensor, e.g., a sensor able to determine an electric field or other electrical characteristic. For example, the sensor may detect capacitance, inductance, etc., of a fluid and/or the portion of the fluidic system containing the fluid. In some cases, the sensor may be connected to a processor, which in turn, cause an operation to be performed on the fluidic droplet, for example, by sorting the droplet.

Characteristics determinable with respect to the fluid and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, or pressure. In certain embodiments, one or more channels in the microfluidic modules include one or more pressure sensors.

A corresponding signal is then produced, for example indicating that "yes" the characteristic is present, or "no" it is not. The signal may correspond to a characteristic qualitatively or quantitatively. That is, the amount of the signal can be measured and can correspond to the degree to which a characteristic is present. For example, the strength of the signal may indicate completeness of a reaction. In response to the signal, data can be collected and/or a control system of sorting feature in a microfluidic module, if present, can be activated to divert fluid flow into one branch channel or another for delivery to the droplet-on-demand portion of the system. The means of changing the flow path can be accomplished through mechanical, electrical, optical, or some other technique as described herein.

An exemplary detector/sensor is an optical detector, which may be coupled with a computer and/or other image processing or enhancement devices to process images or information produced by the optical detector using known techniques. There is no limit to the kind or number of characteristics that can be identified or measured using the techniques of the invention.

In certain embodiments, the detection module may include an apparatus to cause a reagent or chemical intermediate or chemical product to emit measurable light energy, e.g., a light source such as a laser, laser diode, light emitting diode (LED), high-intensity lamp, (e.g., mercury lamp), and the like. Where a lamp is used, the channels are preferably shielded from light in all regions except the detection module. Where a laser is used, the laser can be set to scan across a set of detection modules from different analysis units. In addition, laser diodes or LED's may be microfabricated into the same chip that contains the analysis units. Alternatively, laser diodes or LED's may be incorporated into a second chip (i.e., a laser diode chip) that is placed adjacent to the analysis or microchip such that the laser light from the diodes shines on the detection module(s).

An integrated semiconductor laser and/or an integrated photodiode detector can be included on the chemical production unit, associated with one or more microfluidic modules. This design provides the advantages of compactness and a shorter optical path for exciting and/or emitted radiation, thus minimizing distortion and losses. Fluorescence produced by a reporter, reagent, chemical intermediate, or chemical product, is excited using a laser beam.

Heating and Cooling Elements

In certain embodiments, a microfluidic module will include one or more heating elements. An exemplary heating element is a Peltier device. Peltier devices are commercially available, for example, from Custom Thermoelectric (Bishopville Md.). Peltier devices, also known as thermoelectric (TE) modules, are small solid-state devices that function as heat pumps. Generally, the device is formed by two ceramic plates with an array of small Bismuth Telluride cubes in between. Application of a DC current moves heat from one side of the device to the other, thus producing a temperature gradient in which a first side to which the device is connected is cooled and a second side to which the device is connected is heated. Changing the polarity across the surfaces, reverses the heating/cooling. To increase the efficiency of the Peltier module, a thermal interface material can be placed between the Peltier module and the surface. Exemplary thermal interface materials include silicone-based greases (e.g., zinc oxide silicone), elastomeric pads, thermally conductive tapes, and thermally conductive adhesives.

Peltier devices require that the heat generated from the hot side be removed from the device. In certain embodiments, the peltier device generally includes a heat sink couple to a fan to remove heat from the surface of the device.

In certain embodiments, a microfluidic module will include one or more cooling elements. In certain embodiments, a single unit can have heating and cooling functions and therefore the heating and cooling elements are combined into a single unit. An exemplary device ins a chiller plate that is operably coupled to the microfluidic channel of the microfluidic module. The chiller plate cools the content of the channels.

In certain embodiments, the microfluidic module including a heating and/or cooling element also includes a temperature sensor and/or a temperature controller. The temperature controller and sensor are operably coupled to each other and the sensor is operably coupled to the heating/cooling device and the microfluidic module. The peltier device includes a polarity controller. Any polarity controller known in the art may be used, such as an H-bridge controller (commercially available from Texas Instruments, manufacturer part number DRV8828PWP). The polarity controller is coupled to the temperature sensor. The polarity controller changes polarity of the peltier device in response to a signal sent from the temperature sensor. Changing the polarity changes the heating/cooling of the surface. For example, if the peltier device is configured such that the top portion of the surface is heating and the bottom portion is cooling, then changing the polarity will cause the top portion to cool and the bottom portion to heat.

The entire module can be controlled by any known commercially available controller, such as a programmable logic controller (PLC) or a computer running an operating system such as Windows. Particularly, the temperature sensor sends signals to the logical controller, which then takes the appropriate action (e.g., heating or cooling), based on the signal received from the temperature sensor.

The skilled artisan will recognize that other heating/cooling elements can be used with microfluidic modules, such as those described in Miralles et al. (Diagnostics (Basel). 2013 March; 3(1): 33-67), the content of which is incorporated by reference herein in its entirety.

The microfluidic module can be configured to have one or more temperature zones, e.g., one zone, two zones, three zones, four zones, five zones, etc. The channel or channels within the microfluidic module can be configured to facilitate flow into the one or more temperature zones. For example, a serpentine configuration may be useful when a microfluidic module includes more than one temperature zone (as shown in FIG. 1B). In such a configuration, the microfluidic module can have a first zone at a first temperature along a top of the microfluidic module and a second zone at a second temperature along a bottom of the microfluidic module. Fluid flows through the serpentine channel, moving between the two temperature zones. The number zones will depend on the type of reaction being conducted within the microfluidic module.

Droplet Module

The systems of the invention include a droplet dispenser fluidically coupled to the chemical product production unit that forms and dispenses droplets of the chemical product. Droplet-on-demand technology is described for example in Harris et al. (Exp Fluids (2015) 56:83), the content of which is incorporated by reference herein in its entirety. In certain embodiments, a piezoelectric droplet-on-demand generator is used that is capable of producing droplets of highly repeatable size The generator is low cost and simple to fabricate. Droplet diameter can be controlled through variation of the piezoelectric driving waveform parameters, outlet pressure, and nozzle diameter.

Figure 9:
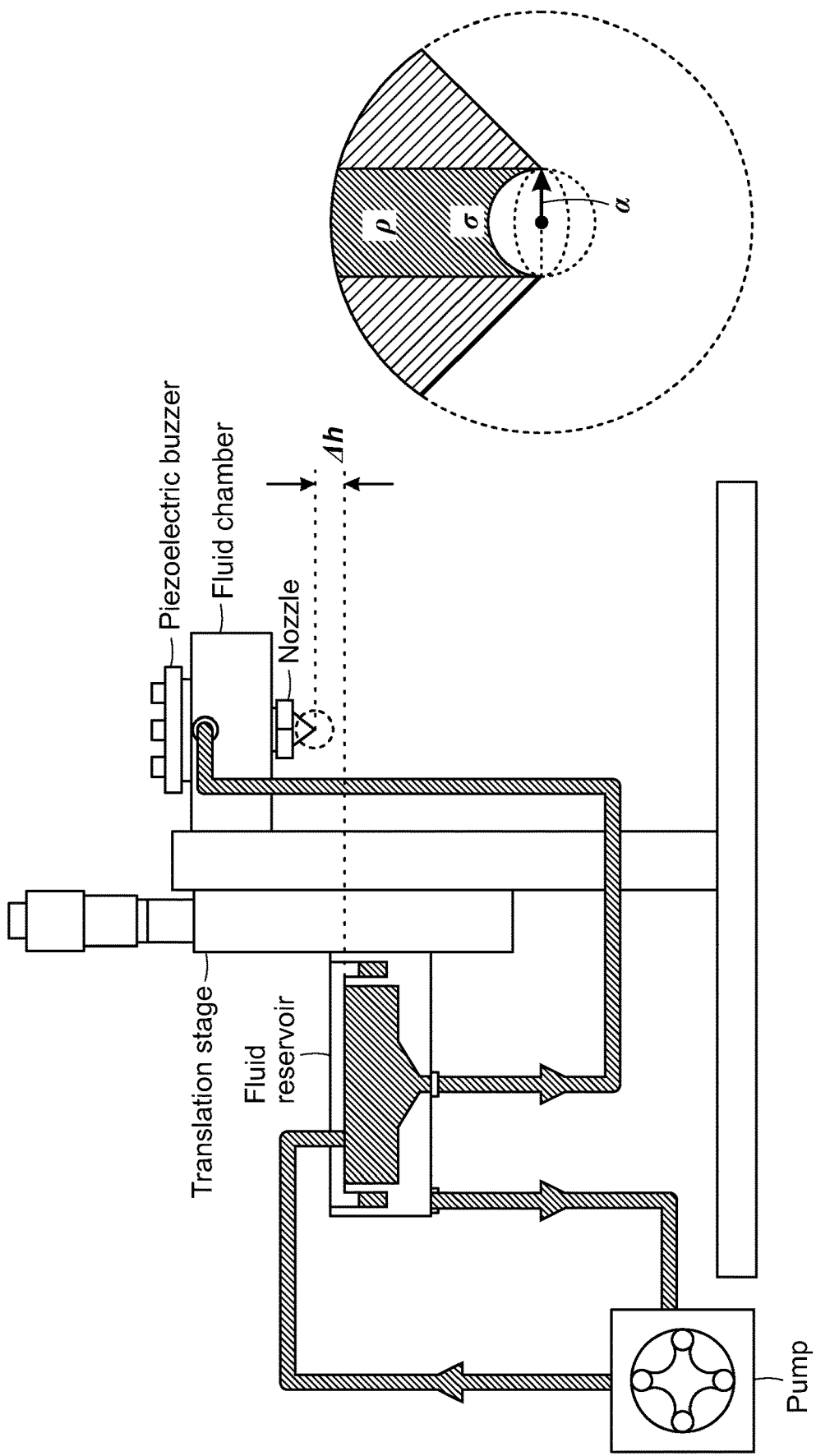
FIG. 9 is a schematic of a droplet generator. Inset the form of the static meniscus at the nozzle outlet depends on h, the difference between the reservoir and nozzle heights. As h increases, the fluid recedes into the nozzle. Stable static menisci arise for $|\Delta| \leq 2\sigma/\rho g a$. The schematic is not drawn to scale.

The droplet generator may include five main components: piezoelectric disk, fluid chamber, nozzle, adjustable-height fluid reservoir, and fluid pump (FIG. 9). The piezoelectric actuator is a commercially available piezoelectric buzzer (CUI CEB-35D26, diameter 35 mm, available at Digi-Key: 102-1128-ND). To create an airtight seal between the piezoelectric and fluid chamber orifice, the piezoelectric is first bonded to the top of the fluid chamber with an RTV silicone sealant and then secured in place by an acrylic ring that provides a clamping force on the edges of the piezoelectric. The brass base of the piezoelectric disk is in direct contact with the working fluid; consequently, a pressure pulse is generated in the fluid chamber by the voltage-induced flexure of the disk.

The electrical components used for driving the piezoelectric element include an adjustable DC power supply (0-72 V), H-bridge circuit, and Arduino Uno microcontroller. The piezoelectric piece is driven by a square voltage waveform. When not in use, the piezoelectric piece is supplied with a constant negative voltage. The sudden application of a positive voltage causes the piezoelectric piece to contract and generates a positive pressure pulse in the chamber that forces liquid through the nozzle. Reverting to a negative voltage causes the piezoelectric to expand and creates a negative pressure fluctuation that draws liquid back into the chamber. Under the right operating conditions, this sequence of expansion and contraction expels a single droplet from the nozzle. While studies have been done on the effect of driving waveform shape on droplet generation (Chen and Basaran 2002; Dong et al. 2006, the content of which is incorporated by reference herein in its entirety), this embodiment employs a square waveform in order to simplify the required circuitry.

Other droplet generators that can be used with systems of the invention are described for example in Jakiela et al. (Micromachines 2014, 5, 1002-1011); Andrukh et al. (Langmuir, 2011, 27 (6), pp 3206-3210); and Fan et al., (Sensors and Actuators A: Physical; Volume 147, Issue 2, 3 Oct. 2008, Pages 649-655), Icten et al., (*Journal of pharmaceutical sciences* 104.5 (2015): 16414649), the content of each of which is incorporated by reference herein in its entirety. In certain embodiments, the droplet generator uses ink-jet printing technology for personalized droplet generation, such as described for example in Alomari et al. (*International journal of pharmaceutics* 494.2 (2014): 568-577), the content of which is incorporated by reference herein in its entirety.

The viscosity and surface tension of any solvent mixture are very important. The surface tension should be high enough to enable the formation of spherical droplets and to resist leakage from the print head when the printer is not in operation. The viscosity should be low enough that the fluid can be jetted but sufficiently high that it is not ejected to early, which can lead to the formation of a tail, producing satellite droplets. Satellite drops (also known as secondary drops) not only affect formation of the primary droplet, but may also impact the location of drug deposition on the substrate. It is important that drops land in their designated coordinate on the substrate, because otherwise dose uniformity cannot be assured. Ideally a satellite drop would recombine with the primary drop or fall not far away on the substrate. Viscosity and surface tension also affect the refilling phase of the drop generator as the solution passes through spouts into the nozzle firing chambers.

Excipients may be added to the solvent to obtain a solution with suitable viscosity and surface tension. Glycols such as propylene glycol (PG), polyethylene glycol (PEG) and glycerol are the most commonly used viscosity modifiers. These excipients, or other additives associated with formulating pharmaceutical formulations, may be introduced to the chemical product in the droplet dispensing unit or in one of the microfluidic modules prior to the droplet dispensing unit.

The droplet generator can be configured to be on a moving arm so that the droplet generator can move along a stationary substrate to dispense droplets of the chemical product onto the substrate. In other embodiments, the droplet generator is held stationary and the substrate is set on a moving stage that can move in the x, y, and/or z direction. While not required, in most embodiments, the substrate and the droplet dispenser will be operably coupled to a computer so that droplet generation and dispensing occurs in a coordinated manner on the substrate.

Dosing herein refers to amount of a chemical product within a single droplet size. Accordingly, dosing (i.e., amount of the chemical product) can be adjusted by adjusting droplet size. In that manner, the system of the invention can operate for personalized dosing. A central controller or computer (discussed further herein), can be loaded with personalized medical information. Mainly, the information will include type of chemical product and amount required per single dose. The system stores that information and when required to dispense a single droplet, the size of the droplet is determined to dispense the correct amount of chemical product per droplet, based on the personalized requirements of the individual. Droplet size can be varied per droplet so that a single substrate can produce droplets of different sizes, e.g., different dosages. If desired, the same droplet size, same dosage, can be dispensed repeatedly on a single substrate. This approach allows for personalized droplet dispensing. Dosage optimization and personalization is further described for example in Jayachandran et al., (PloS one 10.7 (2015): e0133244) and Alomari et al. (*International journal of pharmaceutics* 494.2 (2014): 568-577), the content of each of which is incorporated by reference herein in its entirety.

Sensors, such as optical sensors, such as video cameras, can be used to monitor the droplet generator and provide feedback as to droplet size to the central processor to ensure that the system is operating properly. The feedback can be used in a loop to cause the central processor to send a signal that adjusts the droplet size from the droplet dispenser based on the data being received from the one or more sensors.

Substrates may be an administrable carrier on which the drug solution is printed. For oral administration it is important that the substrate can be ingested. While the ability to jet many drugs has been demonstrated, some studies do not deposit the active onto substrates fit for human consumption. Table 1 lists the substrates used in the literature. The use of a range of different substrates, including edible substrates such as icing sheets, polymeric and starch films and non-edible substrates, such as paper and acetate, has been reported.

TABLE 1

Substrates used for medicine printing as reported in the literature

Hydroxypropyl methyl cellulose (HPMC) films
Edible icing sheets
Uncoated paper, coated paper, and polyethylene terephthalate (PET) film
Glass cover slip coated in flutec fluid to increase hydrophobicity
Orodispersible films, copy paper, water impermeable transparency films
Icing sheet, PET film, HPC film
Clear acetate film, starch film
Uncoated wood-free paper, triple-coated inkjet paper, double-coated sheet
PTFE films over a clear transparency film
Copy paper and photocopy paper Drying helps in reducing the solvent content and enhances the uniformity of printed doses. In traditional printing on paper, absorptive drying is the main mechanism at ambient conditions as the liquid penetrates the fiber network of the papers. Evaporative drying could also be employed to further shorten the drying time using hot air convection, keeping temperatures below 50° C. for sensitive materials. It would also be possible to heat the substrate itself. It is important to investigate the effect of drying on the physical state of the active, if any, and its effect on the therapeutic outcome of the drug.

Valves

Any of the channels in the microfluidic modules can be equipped with one or more valves for flow control. Exemplary valves are rotary valves, but the skilled artisan will recognize that other valves can be used with systems of the invention, such as those described for example in Lee at al. (U.S. patent application publication number 2007/0141593), Neukermans et al. (U.S. Pat. No. 6,068,751), or Unger et al. (Science Vol 288 7 Apr. 2000), the content of each of which is incorporated by reference herein in its entirety. The valves are operably coupled to the central processor, which controls operation of the valves.

Central Processor

Figure 10:
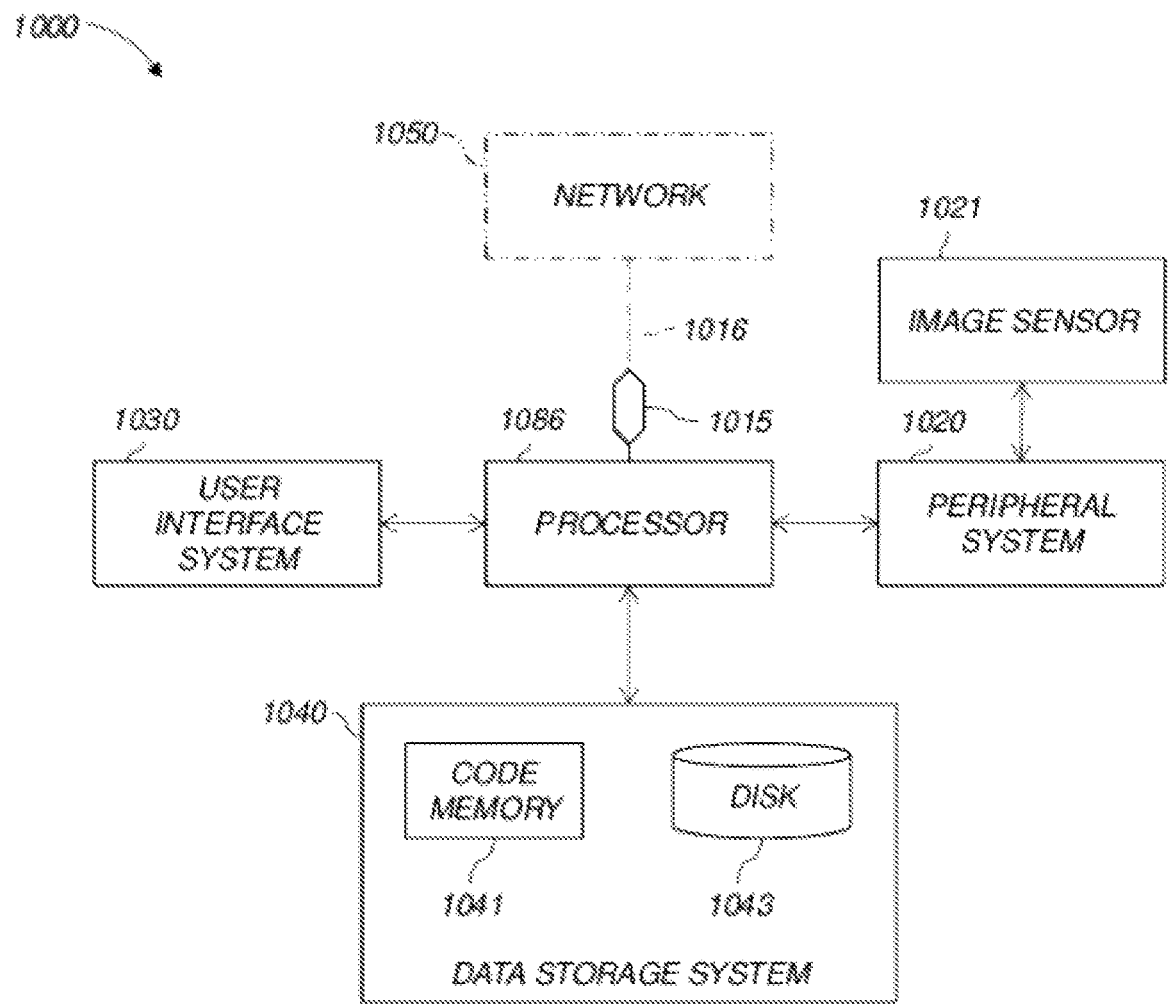
FIG. 10 shows a high-level diagram of the components of an exemplary data-processing system for analyzing data and performing other analyses described herein, and related components.

FIG. 10 is a high-level diagram showing the components of an exemplary data-processing system 1000 for analyzing data and performing other analyses described herein, and related components. The system includes a processor 1086, a peripheral system 1020 (chemical production system), a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), e.g., the Internet or a leased line, as discussed below. The data described above may be obtained using detector 1021 and/or displayed using display units (included in user interface system 1030) which can each include one or more of systems 1086, 1020, 1030, 1040, and can each connect to one or more network(s) 1050. Processor 1086, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 1086 which in one embodiment may be capable of real-time calculations (and in an alternative embodiment configured to perform calculations on a non-real-time basis and store the results of calculations for use later) can implement processes of various aspects described herein. Processor 1086 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. The phrase "communicatively connected" includes any type of connection, wired or wireless, for communicating data between devices or processors. These devices or processors can be located in physical proximity or not. For example, subsystems such as peripheral system 1020, user interface system 1030, and data storage system 1040 are shown separately from the data processing system 1086 but can be stored completely or partially within the data processing system 1086.

The peripheral system 1020 can include one or more devices configured to provide digital content records to the processor 1086. For example, the peripheral system 1020 can include digital still cameras, digital video cameras, cellular phones, or other data processors. The processor 1086, upon receipt of digital content records from a device in the peripheral system 1020, can store such digital content records in the data storage system 1040.

The user interface system 1030 can include a mouse, a keyboard, another computer (e.g., a tablet) connected, e.g., via a network or a null-modem cable, or any device or combination of devices from which data is input to the processor 1086. The user interface system 1030 also can include a display device, a processor-accessible memory, or any device or combination of devices to which data is output by the processor 1086. The user interface system 1030 and the data storage system 1040 can share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 to network 1050. Network link 1016 can be connected to network 1050 via a switch, gateway, hub, router, or other networking device.

Processor 1086 can send messages and receive data, including program code, through network 1050, network link 1016 and communication interface 1015. For example, a server can store requested code for an application program (e.g., a JAVA applet) on a tangible non-volatile computer-readable storage medium to which it is connected. The server can retrieve the code from the medium and transmit it through network 1050 to communication interface 1015. The received code can be executed by processor 1086 as it is received, or stored in data storage system 1040 for later execution.

Data storage system 1040 can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or non-volatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), Universal Serial Bus (USB) interface memory device, erasable programmable read-only memories (EPROM, EEPROM, or Flash), remotely accessible hard drives, and random-access memories (RAMs). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043. Processor 1086 then executes one or more sequences of the computer program instructions loaded into code memory 1041, as a result performing process steps described herein. In this way, processor 1086 carries out a computer implemented process. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects. These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors) to cause functions, acts, or operational steps of various aspects herein to be performed by the processor 1086 (or other processor). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

As illustrated in FIG. 1C, the processor is controls all aspects of the chemical production system. That is, the processor is operably coupled to each of the microfluidic modules, any reservoirs, all sensors, all valves, the droplet dispenser, and any element of the chemical system. Data is sent and received by the processor. The system can be configured to have a feedback loop architecture so that data received by the processor (e.g., by one or more sensors) can be acted on by the user (through manual adjustment via the processor) or processor (in automated embodiments) to correct or adjust one or more operating parameters of the system.

As discussed above, the processor can store data for individual medical files so that information for personalized dosing can be loaded and stored by the processor. The processor then acts on that data and controls the system to generate personalized dosing as discussed above based on the needs within a specific medical file stored on the system.

Microfluidic Reaction Module

An exemplary reaction module is a module that allows chemicals to interact with each other and thereby undergo a chemical reaction. Numerous configurations are possible. In one embodiment, reagents are premixed and loaded into a channel of the reaction module in which an external force (e.g., pressure change, temperature change, light (e.g., UV light through an optically clear portion of the channel), etc.) is used to trigger a start of a reaction. In another embodiment, individual reagents are individually loaded into a channel from different reservoirs, under valve control (FIG. 1B). When the reagents interact with each other, a chemical reaction is initiated. That reaction can then be further controlled via changes in temperature, light, and/or pressure within the microfluidic module. One or more additional reagents can be loaded into the module using one or more branch channels (FIG. 1B). The branch channels can be coupled to a reservoir or have an inlet for a syringe for manual loading (FIG. 1B). The additional reagent is then introduced at a pre-determined location downstream of where the introduction of the prior reagents occurred (FIG. 1B). Again, temperature, light, and/or pressure can continue to be modulated after introduction of the additional reagent. Sensors can be located throughout the module to monitor the progress of the chemical reaction. That information is sent to the processor, and the processor can use the information to control introduction of the reagents to the channel of the reaction module (through sue of valves or flow control).

It may be desirable to cause mixing to occur within the channel to facilitate the chemical reaction. Various channel architectures can be used to facilitate mixing of reagents within channels. Exemplary architectures are described for example in Ismagilov et al. (U.S. patent application publication number 2011/0177494), Link et al. (U.S. patent application publication number 2013/0183659), the content of each of which is incorporated by reference herein in its entirety.

The invention contemplates embodiments that include only a single microfluidic reactor module or embodiments that include a plurality of microfluidic reactor modules (in parallel or in series). A parallel arrangement of modules is helpful for conducting a same reaction ion multiple modules that then feed into a common downstream microfluidic module. FIG. 1A shows a plurality of microfluidic reactor modules in series in which a first reaction occurs in a first microfluidic reactor module and a second reaction occurs in a second microfluidic reactor module. The skilled artisan will appreciate that any number of microfluidic reactor modules can be coupled to each in parallel and/or in series, depending on the reaction to be conducted.

Microfluidic Crystallization Module

Numerous configurations are possible for a crystallization module. An exemplary configuration is shown in FIG. 1B in which the crystallization microfluidic module is configured to generate air-segmented droplets of a first fluid that contain a chemical intermediate or a chemical product in a second fluid that is immiscible with the first fluid. This is a droplet based approach to crystallization in which the crystallization reaction occurs in the droplets of the first fluid that include the chemical intermediate or chemical product while the first fluid is carried by the second immiscible fluid.

Details for microfluidic droplet formation and crystallization within droplets are described for example in Ismagilov et al. (U.S. patent application publication number 2011/0177494), Ismagilov et al. (U.S. patent application publication number 2014/0202546), and Link et al. (U.S. patent application publication number 2013/0183659), the content of each of which is incorporated by reference herein in its entirety.

Droplet formation can occur by using, for example a junction of two channels within a microfluidic module. Exemplary junctions are T junctions, Y junctions, or any angle at which two channels intersect. The first fluid including the chemical intermediate or chemical product flows through one of the channels and an immiscible carrier fluid, such as oil, flows through the other channel. Portions of the first fluid are sheared by the second fluid, including gas, to form droplets of the first fluid in the second fluid. The droplets of the first fluid, including the chemical intermediate or chemical product then flow through the channel and the crystallization reaction occurs within the droplets. It may be desirable to include one or more surfactants in the second fluid, such as described for example in Ismagilov et al. (U.S. patent application publication number 2014/0202546), and Link et al. (U.S. patent application publication number 2013/0183659), the content of each of which is incorporated by reference herein in its entirety.

Figure 4B:
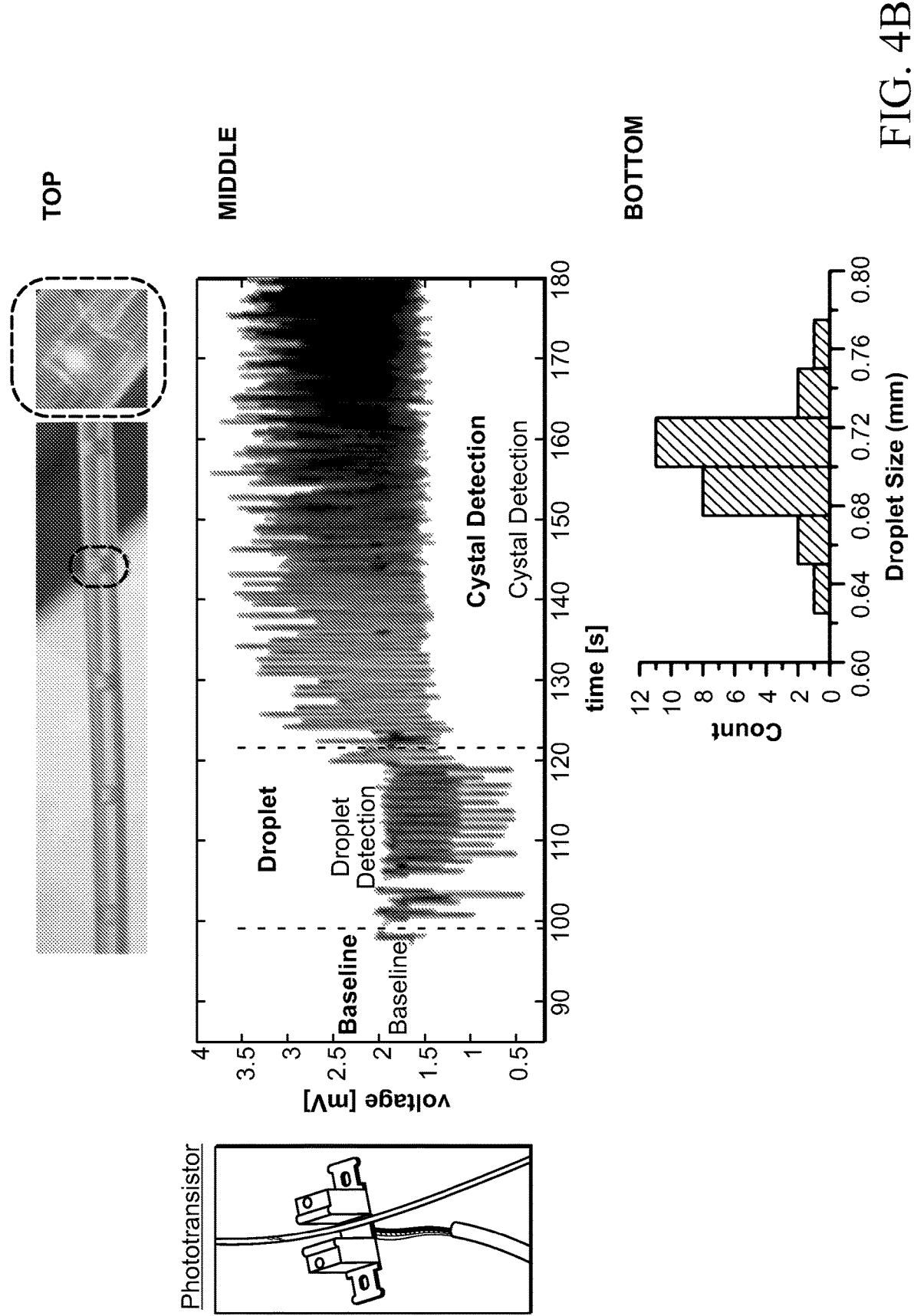
FIG. 4B shows another example of monitoring within the system. The figures show that droplet crystal slurry can be monitored using a video microscope and a phototransistor.

As shown in FIGS. 1B and 4B, a sensor (e.g., video camera or phototransistor), may be used to monitor the crystallization process occurring within the droplets. In such embodiments, at least a portion of the channel, or all of the channel, is optically clear.

Upon completion of the crystallization reaction, it may be desirable to separate the second fluid (oil) from the first fluid including the chemical intermediate or chemical product. Numerous approaches are within the scope of the invention and any one or more of these approaches can be integrated into the crystallization module. In one embodiment, the main channel includes side branch channels. The side branch channels can be used to remove the second fluid (e.g., oil) from between the droplets of the first fluid, bringing the droplets of the first fluid together so that they merge and form a single flow of first fluid. Such an approach is described foe example in Ismagilov et al. (U.S. patent application publication number 2014/0202546), the content of which is incorporated by reference herein in its entirety. In another embodiment, a separation chamber may be used. Typically, the first fluid and the second fluid will have different densities. In that manner, the second fluid including the droplets of the first fluid can be flowed into a vertical chamber. In that chamber, the droplets of the first fluid will separate from the second fluid due to density differences. A first outlet channel is positioned to receive the first fluid including the chemical intermediate or chemical product and a second outlet is positioned to receive the second fluid. In embodiments that use oil, typically the oil will be more dense than the first fluid including the chemical intermediate or chemical product. In the separation chamber, the oil will sink to the bottom of the chamber while the first fluid will rise to the top of the chamber. The first outlet on the top portion of the chamber will receive the first fluid and the second outlet on the bottom portion of the chamber will receive the second fluid. Such an approach is described for example in Link et al. (U.S. Pat. No. 9,562,837) and Link et al. (U.S. patent application publication number 2013/0183659), the content of each of which is incorporated by reference herein in its entirety.

Once separated, the first fluid including the chemical intermediate or chemical product can proceed to another microfluidic module or to the droplet generator.

Microfluidic Filtration Module

Numerous configurations are possible for a filtration module. An exemplary configuration uses micropillar arrays, feed channels, side channels and nano-gap structures, such as described for example in Chen et al. (Electrophoresis, Volume 30, Issue 18, September 2009, Pages 3168-3173), the content of which is incorporated by reference herein in its entirety.

Another exemplary embodiment uses separation packing material, such as sepharose, within a channel of the filtration module. Pressure or another force can be used to drive flow through the separation material and thereby filter the content of the fluid. The separation material can be functionalized to preferentially retain the chemical product or chemical intermediate, allowing unwanted reactants or byproducts to flow through the material. In other embodiments, the unwanted reactants or byproducts are retained in the filtration material and the chemical intermediate or chemical product flows through. An eluting agent can then be introduced to elute any material retained in the filtration material. The eluting agent may be introduced by a syringe or from a reservoir connected to a branch channel that a fluidically coupled to the main channel, upstream of the filtration material.

Typically a valve and a sensor will be positioned after the filtration material and can monitor the content of the material downstream of the filtration material. The valve can be connected to a waste line and a channel that flows to another module or the droplet dispenser. The sensor determines when byproduct or unused reactants are flowing down stream of the filtration material and signals system to have the valve direct that flow to the waste line. When the sensor detects the desired chemical product or chemical intermediate, the flow is changed by the valve to send that material to either another microfluidic module or the droplet dispenser.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Production of Lisinopril Dihydrate

FIG. 1A shows an chemical production unit including a plurality of microfluidic modules configured for production of Lisinopril dihydrate. The modules are all fluidically connected to each other to allow flow between the modules. In this embodiment, the modules of the chemical production unit include: two reactor modules coupled in series, a first crystallization module, a first filtration module, a third reaction module, a second crystallization module, and a second filtration module.

In the first reaction module, Lisinopril ester is introduced through a first inlet port and NaOH is introduced through a second inlet port. The first and second inlet ports are coupled to a microchannel within the microfluidic reactor module. The Lisinopril ester and NaOH mix within the serpentine shaped channel as the reactants flow through the channel. The reactants then flow to the second reaction module.

In the second reaction module an acidification reaction occurs via an introduction of HCl to the mixture of Lisinopril ester and NaOH. Again, mixing is facilitated by the serpentine shape of the microfluidic channel.

The reactants are then flowed to the first crystallization module. Crystallization is triggered via the addition of EtOH. The contents then flow to the first filtration module where purification occurs. The contents then flow to a second reactor module where NaOH is introduced into the channel to cause a neutralization reaction. The second crystallization then occurs in the second crystallization module, using cooling to cause precipitation. A final filtration occurs in the second filtration module, resulting in the production of Lisinopril dihydrate.

The Lisinopril dihydrate can then be flowed to the droplet generation and dispensing unit, as described above, for production of dosages of Lisinopril dihydrate.

Example 2: Production of Diphenhydramine Hydrochloride

A 19.5 μL reactor chip equipped with staggered oriented ridge (SOR) mixing sections was used for this. The SOR sections of the chip create turbulent flow immediately upon mixing two reagents to provide rapid and efficient mixing. The outlet of the reactor chip is fed into a pressure sensor and back pressure regulator (BPR) that was used to run reactions at pressures ranging from 10-20 bar. The first routes explored with this reactor system used either bromo- or chlorodiphenylmethane reacting with dimethylaminoethanol (DMAE) in ACN, a route previously reported in flow.

A 2.0 M solution of the halo-diphenylmethane was mixed with neat DMAE in the first SOR section of the chip and acetonitrile dilution was performed prior to the second SOR section as a reaction quench. We first explored the temperature dependence of this reaction by screening temperatures from 60-200° C. at a residence time of 5.0 min. A strong dependence on temperature was observed with no significant product being formed below 150° C. for both bromo- and chlorodiphenylmethane. While conducting reactions at temperatures higher than 200° C. would be advantageous to potentially optimize the process further, this was not possible due to technical limitation of the commercial system.

In order to develop a completely continuous and automated process, we designed a system capable of seamlessly transitioning between synthesis, analytics, and ultimately purification of the final product. The purification system has been designed as a flexible miniaturized pharmaceutical platform, so that the appropriate purification module, such as extraction and/or crystallization, can be implemented easily and optimized depending on the synthesis being conducted. For the synthesis of diphenhydramine from chlorodiphenylmethane, we have utilized an air-segmented flow crystallizer in addition to the on-line MS capabilities described above.

Crystallization in segmented droplets allows for the continuous crystallization of material at a controlled crystal size without fouling. A full engineering diagram of the experimental setup is detailed in FIG. 1B.

Again using a 19.5 µL reactor chip, the outlet was fed into a valve capable of splitting the flow between collection, waste, MS, and the air-segmented flow crystallizer. As shown in FIG. 5, the system consists of PFA tubing connected in a T-junction to a syringe pump filled with EtOAc, the outlet of the microreactor, and a 0.3 m length of PFA tubing where mixing takes place by diffusion. The EtOAc served as the anti-solvent prior to droplet formation. At this point, there is a high potential for crystal formation that could block the tubing shortly after anti-solvent mixing. We have, therefore, implemented cut-to-length tubing heaters before and after the T-junction to keep the material solubilized and prevent this from occurring. This tubing section is followed by another T-junction, which is connected to the mass-flow controller and a 1.2 m length of PFA tubing where the crystallization takes place. The mass-flow controller is used to modulate the precise flow rate of $N_2(g)$ and in turn create a uniform distribution of $N_2(g)$ segmented droplets.

Multiple analytical techniques were used as PAT to monitor this process, and a LabView based GUI was developed for process integration and automation. A phototransistor was placed in-line to monitor droplet formation. The use of the mass flow controller resulted in uniform droplet distribution that allowed us to control crystal size and prevent fouling of the tubing. The phototransistor was also effective, as shown in FIG. 4B, in detecting crystal formation, and a video microscope was incorporated in-line for the air-segmented flow crystallizer to visualize crystal formation.

What is claimed is:

1. A system for producing a chemical product, the system comprising:
    a chemical product production unit comprising a plurality of microfluidic modules configured to be fluidically coupled to each other in an arrangement that produces a chemical product from an input of a plurality of starting reagents that react with each other due to conditions within the plurality of microfluidic modules through which the starting reagents flow;
    a droplet dispenser fluidically coupled to the chemical product production unit that forms and dispenses droplets of the chemical product; and
    a controller comprising a program configured to implement an anti-fouling algorithm that reduces or eliminates fouling in at least one of the plurality of microfluidic modules.

2. The system according to claim 1, wherein the system comprises one or more sensors.

3. The system according to claim 2, wherein the controller is configured to receive data from the sensors that allow the controller to monitor a process occurring in one or more of the microfluidic modules.

4. The system according to claim 3, wherein the controller is configured to adjust one or more parameters within the one or more of the microfluidic modules based on the received data.

5. The system according to claim 1, wherein the chemical product is a pharmaceutical drug and the controller further comprises a program that determines an optimal drug dosage to be dispensed by the droplet dispenser based on a patient's medical history.

6. The system according to claim 1, wherein the plurality of microfluidic modules are rearrangeable with each other.

7. The system according to claim 1, wherein the chemical production unit is configured to screen one or more chemical pathways prior to production of the chemical product.

8. The system according to claim 1, wherein the plurality of microfluidic modules comprise two or more of a reaction microfluidic module, a purification microfluidic module, a concentration microfluidic module, and a formulation microfluidic module.

9. The system according to claim 1, wherein the system is configured for continuous flow through the chemical product production unit.

10. A method for producing a chemical product, the method comprising:
    providing a system comprising a chemical product production unit that comprises a plurality of microfluidic modules, a droplet dispenser fluidically coupled to the chemical product production unit, a controller comprising a program configured to implement an anti-fouling algorithm that reduces or eliminates fouling in at least one of the plurality of microfluidic modules;
    introducing a plurality of starting reagents to the chemical product production unit;
    flowing the starting reagents through the chemical product production unit, such that a portion of a reaction occurs in each of the plurality of microfluidic modules in order to form a chemical product, under conditions implemented by the anti-fouling algorithm that reduces or eliminates fouling in at least one of the plurality of microfluidic modules; and
    dispensing a droplet of the chemical product using the droplet dispenser.

11. The method according to claim 10, wherein the system further comprises one or more sensors.

12. The method according to claim 11, further comprising monitoring the reaction occurring in one or more of the microfluidic modules via the controller receiving data from the sensors.

13. The method according to claim 12, further comprising adjusting, via the controller, one or more parameters within the one or more of the microfluidic modules based on the received data.

14. The method according to claim 10, wherein the chemical product is a pharmaceutical drug and the method further comprises determining, via the controller, an optimal drug dosage to be dispensed by the droplet dispenser based on a patient's medical history that is received to the controller.

15. The method according to claim 10, wherein the plurality of microfluidic modules are rearrangeable with each other.

16. The method according to claim 10, wherein prior to the introducing step, the method further comprises screening, using the chemical production unit, one or more chemical pathways prior to production of the chemical product.

17. The method according to claim 10, wherein the plurality of microfluidic modules comprise two or more of a reaction microfluidic module, a purification microfluidic module, a concentration microfluidic module, and a formulation microfluidic module.

18. The method according to claim 10, wherein flowing is continuously flowing.

* * * * *